US012104159B2

(12) United States Patent
Chang et al.

(10) Patent No.: US 12,104,159 B2
(45) Date of Patent: Oct. 1, 2024

(54) PIKFYVE ANTISENSE OLIGONUCLEOTIDES

(71) Applicant: AcuraStem Incorporated, Pasadena, CA (US)

(72) Inventors: Wen-Hsuan Chang, Pasadena, CA (US); Emily Elizabeth Lee, Pasadena, CA (US)

(73) Assignee: AcuraStem Incorporated, Pasadena, CA (US)

( * ) Notice: Subject to any disclaimer, the term of this patent is extended or adjusted under 35 U.S.C. 154(b) by 0 days.

(21) Appl. No.: 17/808,247

(22) Filed: Jun. 22, 2022

(65) Prior Publication Data

US 2022/0411804 A1  Dec. 29, 2022

Related U.S. Application Data

(60) Provisional application No. 63/202,717, filed on Jun. 22, 2021.

(51) Int. Cl.
*C07H 21/02* (2006.01)
*A61P 25/00* (2006.01)
*C12N 15/113* (2010.01)

(52) U.S. Cl.
CPC .......... *C12N 15/1137* (2013.01); *A61P 25/00* (2018.01); *C12N 2310/11* (2013.01); *C12N 2310/31* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01); *C12N 2320/32* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 3,687,808 | A | 8/1972 | Merigan, Jr. et al. |
| 6,268,490 | B1 | 7/2001 | Imanishi et al. |
| 6,525,191 | B1 | 2/2003 | Ramasamy |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,547,684 | B2 | 6/2009 | Seth et al. |
| 7,572,582 | B2 | 8/2009 | Wengel et al. |
| 7,666,854 | B2 | 2/2010 | Seth et al. |
| 7,750,131 | B2 | 7/2010 | Seth et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,153,365 | B2 | 4/2012 | Wengel et al. |
| 8,268,980 | B2 | 9/2012 | Seth et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 9,012,421 | B2 | 4/2015 | Migawa et al. |
| 2006/0024715 | A1* | 2/2006 | Liu ..................... C12Q 1/6883 435/6.14 |
| 2008/0039618 | A1 | 2/2008 | Allerson et al. |
| 2015/0191727 | A1 | 7/2015 | Migawa et al. |
| 2020/0199136 | A1 | 6/2020 | Smrcina et al. |
| 2021/0338683 | A1 | 11/2021 | Ichida et al. |
| 2023/0135152 | A1 | 5/2023 | Smrcina et al. |

FOREIGN PATENT DOCUMENTS

| | | |
|---|---|---|
| EP | 3676264 A1 | 7/2020 |
| EP | 4103281 A1 | 12/2022 |
| WO | WO-1999014226 A2 | 3/1999 |
| WO | WO-2004106356 A1 | 12/2004 |
| WO | WO-2007134181 A2 | 11/2007 |
| WO | 2016210372 A2 | 12/2016 |
| WO | WO-2017015555 A1 | 1/2017 |
| WO | 2017070189 A1 | 4/2017 |
| WO | WO-2021163727 A1 | 8/2021 |
| WO | WO-2022271836 A2 | 12/2022 |
| WO | WO-2023215133 A1 | 11/2023 |

OTHER PUBLICATIONS

ISR and Written Opinion issued in PCT/US2022/034539 on Dec. 21, 2022.
Shi, Yingxiao , et al., "Haploinsufficiency Leads to Neurodegeneration in C9ORF72 ALS/FTD Human Induced Motor Neurons", Nature Medicine, Mar. 2018, vol. 24, No. 3, pp. 313-325 (83 pages).
Albaek, N., et al., "Analogues of a locked nucleic acid with three-carbon 2',4'-linkages: synthesis by ring-closing metathesis and influence on nucleic acid duplex stability and structure," J. Org. Chem. 71(20):7731-40, American Chemical Society, United States (Sep. 2006).
Englisch, U., et al., "Chemically Modified Oligonucleotides as Probes and Inhibitors," Angewandte Chemie, International Edition, 30(6):613-29, Wiley-VCH, Germany (Jun. 1991).
Freier, S.M., et al., "The ups and downs of nucleic acid duplex stability: structure-stability studies on chemically-modified DNA:RNA duplexes," Nucleic Acids Research, 25(22):4429-43, Oxford University Press, United Kingdom (Nov. 1997).
Koshkin, A., et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron 54(14):3607-30, Elsevier, Netherlands (Apr. 1998).
Kroschwitz, J.I., "Polynucleotides," in Concise Encyclopedia Of Polymer Science And Engineering, pp. 858-859, John Wiley & Sons, United States (1990).
Kumar, R., et al., "The first analogues of LNA (locked nucleic acids): phosphorothioate-LNA and 2'-thio-LNA," Bioorg. Med. Chem. Lett., 8(16):2219-22, Elsevier, Netherlands (Aug. 1998).

(Continued)

*Primary Examiner* — Amy Rose Hudson
(74) *Attorney, Agent, or Firm* — Sterne, Kessler, Goldstein & Fox P.L.L.C.

(57) ABSTRACT

The present invention relates to PIKFYVE antisense oligonucleotides (ASOs), pharmaceutical compositions containing them, and methods for treating, inhibiting, suppressing, and preventing neurological diseases with them.

39 Claims, 5 Drawing Sheets

Specification includes a Sequence Listing.

(56) References Cited

OTHER PUBLICATIONS

Oka, N., et al., "An oxazaphospholidine approach for the stereocontrolled synthesis of oligonucleoside phosphorothioates," J. Am. Chem. Soc. 125(27):8307-17, American Chemical Society, United States (Jul. 2003).

Sanghvi, Y.S., "Chapter 15: Heterocycle Base Modifications in Nucleic Acids and their Applications in Antisense Oligonucleotides," in Antisense Research and Applications, Crooke, S. T. and Lebleu, B., Eds., pp. 273-288, CRC Press, United States (1993).

Singh, S., et al., "LNA (locked nucleic acids): synthesis and high-affinity nucleic acid recognition," Chem. Commun. 4:455-56, Royal Society of Chemistry, United Kingdom (1998).

Singh, S., et al., "Synthesis of 2'-Amino-LNA: A Novel Conformationally Restricted High-Affinity Oligonucleotide Analogue with a Handle," J. Org. Chem. 63(26):10035-39, American Chemical Society, United States (Nov. 1998).

Srivastava, P., et al., "Five- and six-membered conformationally locked 2',4'-carbocyclic ribo-thymidines: synthesis, structure, and biochemical studies," J. Am. Chem. Soc. 129(26):8362-79, American Chemical Society, United States (Jul. 2007).

Wan, W., et al., "Synthesis, biophysical properties and biological activity of second generation antisense oligonucleotides containing chiral phosphorothioate linkages," Nuc. Acid. Res. 42(22):13456-68, Oxford University Press, United Kingdom (Dec. 2014).

Wils, H., et al., "TDP-43 Transgenic Mice Develop Spastic Paralysis and Neuronal Inclusions Characteristic of ALS and Frontotemporal Lobar Degeneration." PNAS 107(8):3858-63, National Academy of Sciences, United States (Feb. 2010).

International Preliminary Report on Patentability and Written Opinion for International Application No. PCT/US2022/034539, The International Bureau of WIPO, mailed on Jan. 4, 2024, 14 pages.

\* cited by examiner

```
                          SEQUENCE LISTING

<160> NUMBER OF SEQ ID NOS: 534

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atggcatgat ccccataagc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggaccagta caacctgtag                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aggtgcccca acttgttacc                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actaaggtgc cccaacttgt                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
accaggtagt cccaaataac                                                    20

<210> SEQ ID NO 6
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 6
gcctgacccc tatacttgac                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgaccccta tacttgacag                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttaagccctt tggtccaacc                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagttagcac cctctactac                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtcataagtc cttggtcaac                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aagcctgacc cctatacttg                                                   20

<210> SEQ ID NO 12
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 12
agcctgaccc ctatacttga                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catcctatta gcttaaaccc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cctgacccct atacttgaca                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatgatctga tagccaactc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtaccaggac cagtacaacc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caggaccagt acaacctgta                                              20

<210> SEQ ID NO 18
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 18
acaccctttg gagtgtctag                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gccccaactt gttacctaag                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccccaatcta gttcaagcat                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tccaagagtt agcaccctct                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggaccagtac aacctgtagt                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaacccagtg tagctccatt                                                  20

<210> SEQ ID NO 24
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 24
tgccccaact tgttacctaa                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccaatagcaa gcagcctata                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctacaatcaa atcctggtag                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaccaagttt atggacccca                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgaccacca tctatagtta                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctaaggtaac tgttcctaga                                                  20

<210> SEQ ID NO 30
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 30
tgaccaagtt tatggacccc                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accaagttta tggaccccaa                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcaataaagc taaccacatc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gattctacca cacagtacac                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gagccctaac tgtatcttcc                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tagctgattg ccccttaaca                                              20

<210> SEQ ID NO 36
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 36
gagactgcta aggctactac                                                   20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gctaagccct aagtatatcc                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
actactggta aggcagtccc                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggtatcccta cacttctaca                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gagtaccagg accagtacaa                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 ataaccccc tgctaagagc                                                    20

<210> SEQ ID NO 42
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 42
cttagctgat tgccccttaa                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gctatactac tagaagaacc                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtacctaaat acaggtccta                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aggtatccct acacttctac                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcctacatcc agttgattag                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gagtggtaat cagtcctatt                                               20

<210> SEQ ID NO 48
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 48
gacaaagtcc tacctggtac                                                     20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtaatctgtt gagatacacc                                                     20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tccttaatac cccaggttat                                                     20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttccataact aaggtgcccc                                                     20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aactaaggtg ccccaacttg                                                     20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtgccccaac ttgttaccta                                                     20

<210> SEQ ID NO 54
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 54
caagtcccta taacataacc                                                   20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gagcagtcag atgtagttcc                                                   20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaggatggtg taggttccaa                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
taacccacta gaatagcacc                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggtatgccca ccaaagttgt                                                   20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gtacacctta gtctaacagt                                                   20

<210> SEQ ID NO 60
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 60
accaaggtac tctgaaccta                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgagtggtaa tcagtcctat                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62 taccottacc taatcaagag                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gtgagcccta actgtatctt                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 aataacccccc ctgctaagag                                                   20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aaccaatagt gacttatggc                                                    20

<210> SEQ ID NO 66
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 66
ttagctgatt gccccttaac                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agctgattgc cccttaacag                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gctagtttac atacctgtcc                                                  20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ccttaatacc ccaggttatc                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
taactaaggt gccccaactt                                                  20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
taaggtgccc caacttgtta                                                  20

<210> SEQ ID NO 72
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 72
cccaacttgt tacctaagca                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gttggcacat cacactatta                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atgttgaggc tgtcacacta                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctaacctaag gtaactgttc                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aggactagag accacttaac                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acttaacctc cccctacatc                                              20

<210> SEQ ID NO 78
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 78
atggtgtagg ttccaaaccc                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggatctactc ctactactcc                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgacccctat acttgacaga                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cctttggtcc aacctataat                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggtaaaacct gacctatgtc                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agcccaataa tggagttgac                                                    20

<210> SEQ ID NO 84
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 84
gcccaataat ggagttgaca                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttactggaca gatcccttac                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctgagtggta atcagtccta                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agagttagca ccctctacta                                                    20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaatgctgg tcagttgctc                                                    20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
acatagtcca ataccctta                                                     20

<210> SEQ ID NO 90
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 90
actgccatta ggactgttac                                                20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaaagtagtt ggactctccc                                                20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tagttggact ctcccagtgc                                                20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gctccaagta ctatgtcaac                                                20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggatagagga ttcaaggctc                                                20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
taacccccct gctaagagcc                                                20

<210> SEQ ID NO 96
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 96
actcaagaac caacctgtag                                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgctacaacc caactccccc                                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gattgcccct taacagaacc                                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtttagactt gccacactaa                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
taagccctgt cagcacaagg                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggtcttgtag acaccaataa                                                    20

<210> SEQ ID NO 102
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 102
cttaataccc caggttatct                                                  20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ttaatacccc aggttatctc                                                  20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cataactaag gtgccccaac                                                  20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agtggagtac tatggactaa                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcccatactc aagtttatcc                                                  20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caatgttgag gctgtcacac                                                  20

<210> SEQ ID NO 108
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 108
ggcatagctt atggatcaaa                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggctttcact ccaccagatt                                                     20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gacccatctc tcaggtgatc                                                     20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tagcacaggt atccctacac                                                     20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcctgtagcc ctcccctaaa                                                     20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcccagttgg taattccacc                                                     20

<210> SEQ ID NO 114
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 114
cccagttggt aattccaccc                                                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tggtaattcc acccctccaa                                                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggactagaga ccacttaacc                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gaccacttaa cctcccccta                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gagtaccctc caaagaattt                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
atggaagcct gacccctata                                                    20

<210> SEQ ID NO 120
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 120
gccctgaact agataaacac                                                    20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gccctttggt ccaacctata                                                    20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccctttggtc caacctataa                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gacagtaaag gctccacctg                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tcaacaagaa gcctactgac                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
atcataagag ccccaatcat                                                    20

<210> SEQ ID NO 126
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 126
cataagagcc ccaatcatct                                                 20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgatctgata gccaactcaa                                                 20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tcctgagtgg taatcagtcc                                                 20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gacctactac aaactatcag                                                 20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agaccaggtt caatagaatc                                                 20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
agtaccagga ccagtacaac                                                 20

<210> SEQ ID NO 132
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 132
agtccaatac ccttacctaa                                            20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gcatgttaga tccaaatccc                                            20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcccaatagc aagcagccta                                            20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gactgactaa aggaggagcc                                            20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
caaccagtat caatccctc                                             20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tggatagagg attcaaggct                                            20

<210> SEQ ID NO 138
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 138
gtcccagcaa atcaactacc                                               20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtagttacca cctaaacaga                                               20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gatcaccaga ctcaagaacc                                               20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcagcaacct acctgacata                                               20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agcaacctac ctgacatacc                                               20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gcaacctacc tgacatacct                                               20

<210> SEQ ID NO 144
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 144
gacacccttt ggagtgtcta                                               20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ccttagctga ttgcccctta                                               20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
taccatatag gaaacctcct                                               20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ctatactact agaagaaccc                                               20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gtgcccccaa acaagaagtt                                               20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gtacacaaac atccctctaa                                               20

<210> SEQ ID NO 150
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 150
ccatattaca ccttaggaac                                                    20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ccccaacttg ttacctaagc                                                    20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ccaacttgtt acctaagcac                                                    20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcctaaccag tggagtacta                                                    20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
accagtggag tactatggac                                                    20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gtataccatc cacctgagtt                                                    20

<210> SEQ ID NO 156
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 156
gtggcaaaag ttcactactc                                                   20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggtactcttc agatacctaa                                                   20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtacctgaat caagacccac                                                   20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tggtaaggca gtcccaacaa                                                   20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
acaggcatag cttatggatc                                                   20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aggcatagct tatggatcaa                                                   20

<210> SEQ ID NO 162
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 162
tagcacccta aaccatcaat                                                    20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
agcaagtagt tacccttgag                                                    20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tccactatta aggatcttcc                                                    20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gctgccacct agaattaggt                                                    20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ttagcacagg tatccctaca                                                    20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tagcctgtag ccctccccta                                                    20

<210> SEQ ID NO 168
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 168
gttggtaatt ccacccctcc                                                    20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cctacatcca gttgattagc                                                    20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gattcacagg actagagacc                                                    20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aggtgtccaa actaccataa                                                    20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtgtccaaac taccataaac                                                    20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cctaaccagt cagctattag                                                    20

<210> SEQ ID NO 174
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 174 gatcccttc catgtactag                                                    20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gcctagcata tattacccca                                                   20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggagaccact atattatccc                                                   20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gacaaccagc agaatccta                                                    20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggtactatat ccaactggac                                                   20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cattaggtat ggcatgatcc                                                   20

<210> SEQ ID NO 180
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 180
gaacatcact taaatggtcc                                              20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agccctttgg tccaacctat                                              20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gtatgcccac caaagttgtc                                              20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ataccaatgg caaggtttgg                                              20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcaagtggca gcccaataat                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gccaataatc acacccttgg                                              20

<210> SEQ ID NO 186
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 186
acagatccct tacactatca                                               20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atcccataca gccagtttgg                                               20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gcaaccaagg tactctgaac                                               20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
taagtccttg gtcaacttgc                                               20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gatgccacct aaattgctgg                                               20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggattcccag tttaagtcaa                                               20

<210> SEQ ID NO 192
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 192
gaaaggttat ctgttgtgcc                                                    20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193 gactcctat agtcactacc                                                     20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
taccaggacc agtacaacct                                                    20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gaccagtaca acctgtagta                                                    20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggtacaaaag gttccagtag                                                    20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gtacaaaagg ttccagtagc                                                    20

<210> SEQ ID NO 198
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 198
gcttcacata gtccaatacc                                                20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gtccaatacc cttacctaat                                                20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tacctaatca agagaaggtc                                                20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tgaaagtagt tggactctcc                                                20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
aaagtagttg gactctccca                                                20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
acctaagccc acctacaata                                                20

<210> SEQ ID NO 204
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 204
actaagttca gctaccacca                                                 20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205 aaccccctg ctaagagcca                                                  20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gcactgtggc tattacaccc                                                 20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
accatgatgc taccctcagt                                                 20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gccccttgag tgctgtttat                                                 20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
accaggagca tttgttgatc                                                 20

<210> SEQ ID NO 210
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 210
atgctacaac ccaactcccc                                                    20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gctgattgcc ccttaacaga                                                    20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gactgctaag gctactacaa                                                    20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gtgaggatca tgtaacagtc                                                    20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
agtttagact tgccacacta                                                    20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gtgtacctaa atacaggtcc                                                    20

<210> SEQ ID NO 216
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 216
tgcccactga aaccttactc                                                   20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tatgcccatc cctaagttgt                                                   20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ggactatctc taatcagtgg                                                   20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aaggtgcccc aacttgttac                                                   20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tcattgcctt acctaagtac                                                   20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cattgcctta cctaagtaca                                                   20

<210> SEQ ID NO 222
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 222
cagtggagta ctatggacta                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ggagtactat ggactaagaa                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
taagccctaa gtatatcctc                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aagttcacta ctcccaacta                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ggttggcaca tcacactatt                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gtttgcttaa ccaatgctgg                                              20

<210> SEQ ID NO 228
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 228
acagtttgcc taaacctggc                                                    20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
acacaatccc atgataggac                                                    20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
cccccaatct agttcaagca                                                    20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gactacctcc tacttttagt                                                    20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
aagtacctga atcaagaccc                                                    20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ctactggtaa ggcagtccca                                                    20

<210> SEQ ID NO 234
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 234
ggtaaggcag tcccaacaaa                                                    20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttaacagcaa gtagttaccc                                                    20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tcacactaac ctaaggtaac                                                    20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gatctaagag ttaagctctc                                                    20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tagaatactt gacccatctc                                                    20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gcaaccctat gtaagtctat                                                    20

<210> SEQ ID NO 240
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 240
ggctgccacc tagaattagg                                                20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gtatccctac acttctacac                                                20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
aactgttcct cccagttggt                                                20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ccagttggta attccacccc                                                20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ttggtaattc cacccctcca                                                20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggtcaaagac ctgagtcacc                                                20

<210> SEQ ID NO 246
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 246
actcatggag tattactgcc                                                    20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
atggagtatt actgcccccaa                                                   20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
aacctccccc tacatcctat                                                    20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
cccatcacat caagttacag                                                    20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tatgacaatc aatcccaccc                                                    20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gaaattcccc tacccagtcc                                                    20

<210> SEQ ID NO 252
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 252
aattccccta cccagtccta                                                    20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ccctagacag tgtagtagtt                                                    20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ttccaagagt tagcaccctc                                                    20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gtatatccca atgataccag                                                    20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
aaccagtcag ctattagaac                                                    20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gccctgccat caaaaaactc                                                    20

<210> SEQ ID NO 258
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 258
tcaggatcta ctcctactac                                                   20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
caggatctac tcctactact                                                   20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gagccactta cagatgatcc                                                   20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gttattagac acctactctc                                                   20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ctctgtagta gtttaggtgg                                                   20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ggaagcctga cccctatact                                                   20

<210> SEQ ID NO 264
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 264
gaccCCtata cttgacagaa                                               20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ctgccctgaa ctagataaac                                               20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gctaaaactc caatcctatc                                               20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
cctattagct taaacccatc                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
accatttgct agataggtgc                                               20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ggcagcccaa taatggagtt                                               20

<210> SEQ ID NO 270
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 270
gcagcccaat aatggagttg                                                    20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
acaactatga tctgatagcc                                                    20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ggaagctagt tatacaacac                                                    20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
atcagtccta ttaacctacc                                                    20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggttaactta gcttggtctc                                                    20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gacaggattc ccagtttaag                                                    20

<210> SEQ ID NO 276
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 276
acttgagtac caggaccagt                                                   20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cttcacatag tccaataccc                                                   20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttcacatagt ccaataccct                                                   20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
catagtccaa tacccttacc                                                   20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tagtccaata cccttaccta                                                   20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ggctgctcaa tgacaagtgg                                                   20

<210> SEQ ID NO 282
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 282
ggactaaccc agaggtcacc                                                   20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gagtctgcct attcctgatc                                                   20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
agtagttgga ctctcccagt                                                   20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gttcctacag tttaacacag                                                   20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggttccccac caacagaatg                                                   20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tacctaagcc cacctacaat                                                   20

<210> SEQ ID NO 288
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 288
accagtatca ataccctcaa                                                    20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gatgatctca gctagaatcc                                                    20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gatctcagct agaatcctta                                                    20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
atggatagag gattcaaggc                                                    20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
agccctaact gtatcttccc                                                    20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ctaagagtga tgacagttcc                                                    20

<210> SEQ ID NO 294
<211> LENGTH: 20
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 294
ggacacttaa acaggcacta                                            20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 295
gaaaaataac ccccctgcta                                            20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 296
aaaataaccc ccctgctaag                                            20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 297
gactgactcc tatccaacac                                            20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 298
caccctatta tactcagagc                                            20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 299
gtttctagcc ccttgagtgc                                            20

<210> SEQ ID NO 300
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 300
gtaccatata ggaaacctcc                                                    20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
accatatagg aaacctcctc                                                    20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
caagtttaga cttgccacac                                                    20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cctgctgaag ctatactact                                                    20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tactagaaga acccatgagc                                                    20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gatccaggat tatcatacca                                                    20

<210> SEQ ID NO 306
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 306
gcttcaccct tctaggacta                                                    20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gattgctcct accactcttg                                                    20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggttacttca caaactccaa                                                    20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gctgaccaag tttatggacc                                                    20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ggtattacac actcagccta                                                    20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gtattacaca ctcagcctag                                                    20

<210> SEQ ID NO 312
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 312
gtctccttaa tacccaggt                                                    20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cttccataac taaggtgccc                                                   20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggtgccccaa cttgttacct                                                   20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cccctgttct ctaatgtact                                                   20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gcactgccaa gctatcagat                                                   20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tgccaagcta tcagataagc                                                   20

<210> SEQ ID NO 318
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 318
ccagtggagt actatggact                                                 20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ctaatcaatg tgctaagccc                                                 20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gcacagaatt agcccatact                                                 20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gaattagccc atactcaagt                                                 20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cttagaagtc cccaagtcta                                                 20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
cctcaataac catgacaggt                                                 20

<210> SEQ ID NO 324
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 324
tcaggtactc ttcagatacc                                                    20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gctcttacat tcaccagata                                                    20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ttgcttaacc aatgctggtg                                                    20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gcatacagtt tgcctaaacc                                                    20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cacaatccca tgataggact                                                    20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
caatcccatg ataggactat                                                    20

<210> SEQ ID NO 330
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 330
tgtcaaccta acaagttggt                                                    20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gtcaacctaa caagttggtt                                                    20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tactggtaag gcagtcccaa                                                    20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
caccaggtag tcccaaataa                                                    20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ggtagtccca aataactttc                                                    20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
attagcacag gtatccctac                                                    20

<210> SEQ ID NO 336
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 336
gtagccctcc cctaaattct                                                    20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggtaattcca cccctccaac                                                    20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gtcaaagacc tgagtcacct                                                    20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tgtgagagat caactcaaca                                                    20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ggagtattac tgccccaaaa                                                    20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ctagagacca cttaacctcc                                                    20

<210> SEQ ID NO 342
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 342
gagaccactt aacctccccc                                                    20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343 cccctacat cctatcacta                                                     20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ctatagtgta tccagccaat                                                    20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ggatggtgta ggttccaaac                                                    20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gatggtgtag gttccaaacc                                                    20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tgttaccaca tttcagtccc                                                    20

<210> SEQ ID NO 348
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 348
aacttccaag agttagcacc                                                   20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agtaccctcc aaagaatttc                                                   20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gcctaaccag tcagctatta                                                   20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
ccagtcagct attagaacta                                                   20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ggttttgtca agctaacaac                                                   20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ggctgtaatg acctcccctg                                                   20

<210> SEQ ID NO 354
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 354
ctcaggatct actcctacta                                                   20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
aggatctact cctactactc                                                   20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gaagcctgac ccctatactt                                                   20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gtaaaacctg acctatgtcc                                                   20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gcttaaaccc atcaaactga                                                   20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tccaaatggc tgatgtaacc                                                   20

<210> SEQ ID NO 360
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 360
cagcccaata atggagttga                                              20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ggtctgttta ctggacagat                                              20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
cagatccctt acactatcaa                                              20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
atccagacct ttagttacca                                              20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
aatcataaga gccccaatca                                              20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gatctgatag ccaactcaat                                              20

<210> SEQ ID NO 366
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 366
ggatggcaag atcccataca                                               20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gaaccccaag agtgatgacc                                               20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
cctgagtggt aatcagtcct                                               20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
taacctacct acccaaagcc                                               20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gcactagatg gtttgaatac                                               20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gatcaggctc attcacaaca                                               20

<210> SEQ ID NO 372
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 372
gccacaaagt tacctactag                                              20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ggaacttagc atcacattag                                              20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gacagctcca caggtatcaa                                              20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gctattatta gaccaggttc                                              20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gacttgagta ccaggaccag                                              20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ttgagtacca ggaccagtac                                              20

<210> SEQ ID NO 378
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 378
cagttcaagg actagctctt                                                   20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
cacatagtcc aatacccttta                                                  20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
atagtccaat acccttacct                                                   20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ctgccattag gactgttaca                                                   20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
tgccattagg actgttacag                                                   20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
aaggctcacc tataaacaac                                                   20

<210> SEQ ID NO 384
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 384
gtatgaccat ccttacatac                                                   20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aagtagttgg actctcccag                                                   20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
agttggactc tcccagtgcc                                                   20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gtacaggtca ctacagatga                                                   20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
taatatccac tcctacctgg                                                   20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cctacctaag cccacctaca                                                   20

<210> SEQ ID NO 390
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 390
gtgtagctcc atttcaactt                                                   20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ggtgctactt actgaacacc                                                   20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ccctaactgt atcttcccaa                                                   20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
cactggctag tgctttatcc                                                   20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gcaactgtca accaagactg                                                   20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gtaatccagg tcatagttcc                                                   20

<210> SEQ ID NO 396
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 396
ccaatagtga cttatggcat                                                       20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ccaggcagca acctacctga                                                       20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
ggagactgct aaggctacta                                                       20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
agactgctaa ggctactaca                                                       20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gcattaccaa taaatccacc                                                       20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tggtcagtct acccagttaa                                                       20

<210> SEQ ID NO 402
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 402
gcccttctca cattaagcat                                               20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
aattaccatg ccccagagac                                               20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
cctaaataca ggtcctaatg                                               20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
aacatcaatc tgagacaccc                                               20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gttgcctatc ctcacttacc                                               20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
cctcaggtca atctatgcta                                               20

<210> SEQ ID NO 408
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 408
tatgcccact gaaaccttac                                              20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
aggttacttc acaaactcca                                              20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gcccatatta caccttagga                                              20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ataactaagg tgccccaact                                              20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
atcttccact aagaagtccc                                              20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tgctaagccc taagtatatc                                              20

<210> SEQ ID NO 414
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 414
aagccctaag tatatcctca                                              20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gtatctatat gagactccag                                              20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tataccatcc acctgagttc                                              20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gcaaaagttc actactccca                                              20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gttcactact cccaactact                                              20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
aggtactctt cagataccta                                              20

<210> SEQ ID NO 420
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 420
gtccctataa cataacctag                                                 20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
caagtgacca ccatctatag                                                 20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gctagtcaag tctcattaac                                                 20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
ttacacaatc ccatgatagg                                                 20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
acaatcccat gataggacta                                                 20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
cccaatctag ttcaagcatc                                                 20

<210> SEQ ID NO 426
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 426
agatggtgac tacctcctac                                                  20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ctggtaaggc agtcccaaca                                                  20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
taaggcagtc ccaacaaaac                                                  20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
aagcaggacc tgtctgttac                                                  20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gacaggcata gcttatggat                                                  20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ctagattagt gaacagtagc                                                  20

<210> SEQ ID NO 432
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 432
cacactaacc taaggtaact                                                   20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
ccaggtagtc ccaaataact                                                   20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gtagtcccaa ataactttcc                                                   20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
attgccccca gactcctact                                                   20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
ccccagactc ctacttaaac                                                   20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
gagtatagaa tacttgaccc                                                   20

<210> SEQ ID NO 438
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 438
gtaaattagc acaggtatcc                                              20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
actgttcctc ccagttggta                                              20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gttcctccca gttggtaatt                                              20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
ctcccagttg gtaattccac                                              20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
cagttggtaa ttccacccct                                              20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
agttggtaat tccacccctc                                              20

<210> SEQ ID NO 444
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 444
gtaccctgat gataccttc                                                      20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
ggttagaatg gatcaaaacc                                                     20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
gtcaaagtag gtccactgaa                                                     20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
acttccaaga gttagcaccc                                                     20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
accctctact accaagcagt                                                     20

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ggtgtccaaa ctaccataaa                                                     20

<210> SEQ ID NO 450
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 450
ctaaccagtc agctattaga                                                 20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
atcagcaaga gcctattaag                                                 20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
gcaggttcag tgctaagatt                                                 20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
gtaagacttg ctgactcacc                                                 20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
caagtagctg taagtccaac                                                 20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
atccccaaag agacctatgc                                                 20

<210> SEQ ID NO 456
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 456
caaccagcag aatccctata                                                     20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ttaggtatgg catgatcccc                                                     20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
taagcccttt ggtccaacct                                                     20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
aagccctttg gtccaaccta                                                     20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
taccaatggc aaggtttggc                                                     20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
ttgttctggc tgaccaagtc                                                     20

<210> SEQ ID NO 462
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 462
gttctggctg accaagtctg                                               20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tcaccttgac ttaggcaaac                                               20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
ggcaaaccac tccaagttga                                               20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
caagtggcag cccaataatg                                               20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tttactggac agatcccttta                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tactggacag atcccttaca                                               20

<210> SEQ ID NO 468
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 468
ggacagatcc cttacactat                                               20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ctgaacagag tactaaccac                                               20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
ataagagccc caatcatcta                                               20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
cctaaacaca tgaacctggt                                               20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
taatgtagac tggtccaggc                                               20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
aaggagcccc cagttgatct                                               20

<210> SEQ ID NO 474
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 474
gatcccatac agccagtttg                                                   20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
ttgaggcaac caaggtactc                                                   20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
caaccaaggt actctgaacc                                                   20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ccaaggtact ctgaacctaa                                                   20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
agtagaactg tcactatacc                                                   20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
gtaacaacca cccctggaaa                                                   20

<210> SEQ ID NO 480
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 480
ttcctgagtg gtaatcagtc                                                    20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gactacctct attgtcaaca                                                    20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
acaccttgta cttcaagtgc                                                    20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cttagtagtc agaactagcc                                                    20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
ggacagtcta aacagccaca                                                    20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
ggaaaggtta tctgttgtgc                                                    20

<210> SEQ ID NO 486
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 486
aaggttatct gttgtgccac                                                  20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
ggacaaagtc ctacctggta                                                  20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
tgagtaccag gaccagtaca                                                  20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
acccttacct aatcaagaga                                                  20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
taaaggaagc atccccttgt                                                  20

<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
aactgccatt aggactgtta                                                  20

<210> SEQ ID NO 492
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 492
tgagaaaggc tcacctataa                                                   20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
atctatgcct tccaaggatc                                                   20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
gctacagccc aatagcaagc                                                   20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
ggtcatcaga gtctgcctat                                                   20

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
cctgatctaa acccataccc                                                   20

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
gtagttggac tctcccagtg                                                   20

<210> SEQ ID NO 498
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 498
acagacacta gtattgcctc                                               20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
aatatccact cctacctggt                                               20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tggttcccca ccaacagaat                                               20

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
atggcatgat ccccataagc                                               20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
aggaccagta caacctgtag                                               20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
aggtgcccca acttgttacc                                               20

<210> SEQ ID NO 504
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 504
actaaggtgc cccaacttgt                                                   20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
accaggtagt cccaaataac                                                   20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
gcctgacccc tatacttgac                                                   20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ctgaccccta tacttgacag                                                   20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508 ttaagcccttt tggtccaacc                                                  20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
gagttagcac cctctactac                                                   20

<210> SEQ ID NO 510
<211> LENGTH: 20
<212> TYPE: DNA
<213> ORGANISM: Artificial Sequence
<220> FEATURE:
```

<223> OTHER INFORMATION: Description of Artificial Sequence: Synthetic
       oligonucleotide

<400> SEQUENCE: 510
gtcataagtc cttggtcaac                                              20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 511
aagcctgacc cctatacttg                                              20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 512
agcctgaccc ctatacttga                                              20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 513
catcctatta gcttaaaccc                                              20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 514
cctgacccct atacttgaca                                              20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 515
tatgatctga tagccaactc                                              20

<210> SEQ ID NO 516
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 516
gtaccaggac cagtacaacc                                                   20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
caggaccagt acaacctgta                                                   20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518 acacctttg gagtgtctag                                                    20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
gccccaactt gttacctaag                                                   20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ccccaatcta gttcaagcat                                                   20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tccaagagtt agcaccctct                                                   20

<210> SEQ ID NO 522
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 522
ggaccagtac aacctgtagt                                                   20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
aaacccagtg tagctccatt                                                   20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
tgccccaact tgttacctaa                                                   20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ccaatagcaa gcagcctata                                                   20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ctacaatcaa atcctggtag                                                   20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
gaccaagttt atggacccca                                                   20

<210> SEQ ID NO 528
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 528
gtgaccacca tctatagtta                                                     20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
ctaaggtaac tgttcctaga                                                     20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
tgaccaagtt tatggacccc                                                     20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
accaagttta tggaccccaa                                                     20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gcaataaagc taaccacatc                                                     20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gattctacca cacagtacac                                                     20

<210> SEQ ID NO 534
<211> LENGTH: 180
<212> TYPE: DNA
<213> ORGANISM: Unknown
<220> FEATURE:
```

```
<223> OTHER INFORMATION: Description of Unknown:
      C9ORF72 repeat expansion sequence

<400> SEQUENCE: 534
ggggccgggg ccgggccgg ggccggggcc ggggccgggg ccggggccgg ggccggggcc    60
ggggccgggg ccgggccgg ggccggggcc ggggccgggg ccggggccgg ggccggggcc   120
ggggccgggg ccgggccgg ggccggggcc ggggccgggg ccggggccgg ggccggggcc   180
```

PIKFYVE ANTISENSE OLIGONUCLEOTIDES

This application claims the benefit of U.S. Patent Application No. 63/202,717, filed Jun. 22, 2021, which is hereby incorporated by reference.

SEQUENCE LISTING

The instant application contains a Sequence Listing which has been submitted electronically in ASCII format and is hereby incorporated by reference in its entirety. Said ASCII copy, created on Aug. 2, 2022, is named 151421-01602_SL.txt and is 126,748 bytes in size.

FIELD OF THE INVENTION

The present invention relates to PIKFYVE antisense oligonucleotides (ASOs), pharmaceutical compositions containing them, and methods for treating, inhibiting, suppressing, and preventing neurological or neurodegenerative diseases with them.

BACKGROUND OF THE INVENTION

Many neurodegenerative disorders in patients are difficult to effectively treat, especially where the pathology of a neurodegenerative disorder in a particular patient is not completely understood.

International Publication No. WO 2016/210372 discloses a method of treating a neurodegenerative disease by administering a PIKFYVE inhibitor.

There remains a need for effective treatments for many neurodegenerative disorders, such as amyotrophic lateral sclerosis (ALS) and frontotemporal dementia (FTD).

SUMMARY OF THE INVENTION

The present invention relates to PIKFYVE antisense oligonucleotides (ASOs), pharmaceutical compositions containing them, and their use in the treatment of neurodegenerative disorders.

One embodiment is a single stranded ASO that suppresses the expression of PIKFYVE, wherein the ASO has a nucleobase sequence that comprises at least 12 or 15 consecutive nucleobases of any of the nucleobase sequences of SEQ ID NO: 1-500. The nucleobase sequence of the ASO can comprise up to 30, 25, 24, 23, 22, 21, or 20 consecutive nucleobases of any of the nucleobase sequences of SEQ ID NO: 1-500. The ASO can also be any of SEQ ID NO: 1-500.

Another embodiment is an oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NO: 1-500. The oligonucleotide can comprise up to 25, 24, 23, 22, 21, or 20 consecutive nucleobases of any of the nucleobase sequences of SEQ ID NO: 1-500.

In certain embodiments, at least one internucleoside linkage is a modified internucleoside linkage, and the modified internucleoside linkage may be a phosphorothioate internucleoside linkage or a phosphodiester internucleoside linkage. At least one of the nucleosides may also be a modified nucleobase.

In other embodiments, at least one nucleoside of the ASO may be a modified sugar moiety, where that modified sugar moiety can be a bicyclic sugar moiety, or the modified sugar moiety may comprise a 2'-O-methoxyethyl group. In certain aspects, the bicyclic sugar moiety comprises a 4'-CH(R)—O-2' bridge where the R group is, independently, H, $C_{1-12}$ alkyl, or a protecting group.

In yet other embodiments, the ASO is a gapmer (e.g., a MOE gapmer), where a gap segment may consist of 8 to 12 linked deoxynucleosides, a 5' wing segment consisting of 3 to 5 linked nucleosides, and a 3' wing segment consisting of 3 to 5 linked nucleosides. In certain aspects, the gap segment may be positioned between the 5' wing segment and the 3' wing segment, where a nucleoside of each wing segment comprises a modified sugar moiety (e.g., one with a 2'-O-methoxyethyl group).

In other embodiments, the oligonucleotide consists of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NO: 1-500.

Another embodiment is a pharmaceutical composition comprising a PIKFYVE ASO of the present invention and one or more pharmaceutically acceptable carriers, diluents, and/or excipients. In one embodiment, the pharmaceutical composition is suitable for parenteral administration, such as intracerebroventricular injection or intrathecal administration.

Yet another embodiment is a method of inhibiting, suppressing, or preventing expression of PIKFYVE in a patient (such as one having a neurological or neurodegenerative disease) by administering (for example by, intracerebroventricular injection or intrathecal administration) a PIKFYVE ASO or a pharmaceutical composition described herein (for instance, an effective amount thereof) to the patient.

Yet another embodiment is a method of treating a subject having a neurological or neurodegenerative disease by administering a therapeutically effective amount of a PIKFYVE ASO or a pharmaceutical composition described herein. In one embodiment, the disease is amyotrophic lateral sclerosis (ALS) (e.g., C9orf72-associated ALS). In another embodiment, the disease is frontotemporal dementia (FTD), such as FTD with TDP-43 pathology or FTD with tau pathology. In yet another embodiment, the disease is C9orf72-associated FTD (C9-FTD). In yet another embodiment, the disease is microtubule-associated protein tau (MAPT)-associated FTD (MAPT-FTD), such as FTD with the V337M MAPT mutation.

Yet another embodiment is a method of treating a subject having a PIKFYVE disease or disorder by administering a therapeutically effective amount of a PIKFYVE ASO or a pharmaceutical composition described herein.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

Figure 1:
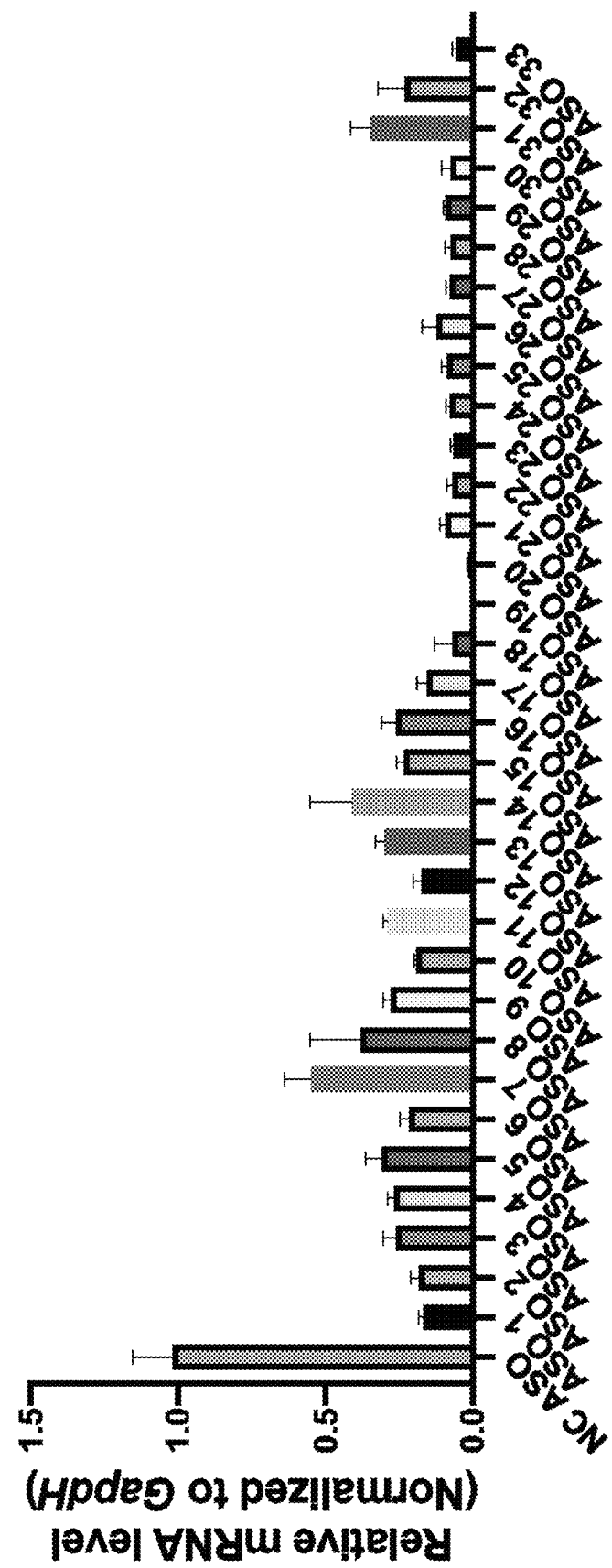
FIG. 1 shows a PIKFYVE ASO screen in HeLa cells, measuring the relative mRNA expression levels of ASO 1-33 (SEQ ID NO: 1-33) against a control (NCASO).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

Definitions

The terms "comprise(s)," "include(s)," "having," "has," "can," "contain(s)," "may" and variants thereof, as used herein, are intended to be open-ended transitional phrases, terms, or words that do not preclude the possibility of additional acts or structures.

The singular forms "a," "an" and "the" include plural references unless the context clearly dictates otherwise.

The present disclosure also contemplates other embodiments "comprising," "consisting of" and "consisting essentially of," the embodiments or elements presented herein, whether explicitly set forth or not.

As used herein, "2'-deoxynucleoside" means a nucleoside comprising a 2'-H(H) furanosyl sugar moiety, as found in naturally occurring deoxyribonucleic acids (DNA) and a nucleobase. In certain embodiments, a 2'-deoxynucleoside may comprise a modified nucleobase and a furanosyl sugar moiety or may comprise an RNA nucleobase (uracil) and a furanosyl sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "antisense molecule" means an oligomeric nucleic acid or oligomeric duplex capable of achieving at least one antisense activity.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety. As used herein, "bicyclic nucleoside" or "BNA" means a nucleoside comprising a bicyclic sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T); adenine (A) and uracil (U); cytosine (C) and guanine (G); and 5-methylcytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyfuranosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications. Table 2, below, provides exemplary MOE-gapmers.

In certain embodiments, oligonucleotides comprise one or more type of modified sugar and/or unmodified sugar moiety arranged along the oligonucleotide or region thereof in a defined pattern or sugar motif. In certain instances, such sugar motifs include, but are not limited to, any of the sugar modifications discussed herein.

In certain embodiments, modified oligonucleotides comprise or consist of a region having a gapmer motif, which is defined by two external regions or "wings" and a central or internal region or "gap." The three regions of a gapmer motif include the "5' wing", the "gap" and the "3' wing" which form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides (e.g., 10 nucleosides). In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

"Inhibit" as used herein refers to the ability to substantially antagonize, prohibit, prevent, suppress, restrain, slow, disrupt, alter, eliminate, stop, or reverse the progression or severity of the activity of a particular agent (e.g., infectious agent) or disease.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate linkage" is a modified internucleoside linkage in which one of the non-bridging oxygen atoms of a phosphodiester internucleoside linkage is replaced with a sulfur atom.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include, but are not limited to, phosphates, which contain a phosphodiester bond (also referred to as unmodified or naturally occurring linkages), phosphotriesters, methylphosphonates or other alkylphosphonates, phosphoramidates, and phosphorothioates, and phosphorodithioates. Representative non-phosphorus containing internucleoside linking groups include but are not limited to methylenemethylimino ($-CH_2-N(CH_3)-O-CH_2-$), thiodiester, thionocarbamate ($-O-C(=O)(NH)-S-$); siloxane ($-O-SiH_2-O-$); and N,N'-dimethylhydrazine ($-CH_2-N(CH_3)-N(CH_3)-$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include, but are not limited to, alkylphosphonates and phosphorothioates. Modified oligonucleotides comprising internucleoside linkages having a chiral center can be prepared as populations of modified oligonucleotides comprising stereo-random internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereo-random. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003); Wan et al., *Nuc. Acid. Res.* 42, 13456 (2014); Chapter 10 of Locked Nucleic Acid Aptamers in Nucleic Acid and Peptide Aptamers: Methods and Protocols v 535, 2009 by Barciszewski et al., editor Gunter Mayerand; and WO 2017/015555. In certain embodiments, a population of modified oligonucleotides is enriched for modified oligonucleotides having at least one indicated phosphorothioate in the (Sp) configuration. In another embodiment, a population of modified oligonucleotides is enriched for modified oligonucleotides having at least one indicated phosphorothioate in the (Rp) configuration.

As used herein, "MOE" means methoxyethyl. "2'-MOE" means a —OCH$_2$CH$_2$OCH$_3$ group at the 2' position of a furanosyl ring.

A "neurological disease" is any disease that causes electrical, biochemical, or structural abnormalities in the brain, spine, or neurons. For example, a neurological disease may be a neurodegenerative disease. The neurodegenerative disease may result in motor neuron degeneration, for example. The neurological disease may be amyotrophic lateral sclerosis (ALS), Huntington's disease, Alzheimer's disease, or frontotemporal dementia, for example. Further examples of neurological diseases include, but are not limited to, Parkinson's disease, multiple sclerosis, peripheral myopathy, Rasmussen's encephalitis, attention deficit hyperactivity disorder, autism, central pain syndromes, anxiety, and/or depression, for example.

The neurological disease may be associated with aberrant endosomal trafficking. For example, endosomal pathways and endosomes are necessary components for the recycling or breakdown of membrane-bound proteins, trafficking of Golgi-associated proteins, and the extracellular release of proteins in exosomes. These processes aid neurotransmission and drive a balance between recycling and degradation of synaptic vesicles or neurotransmitter receptors, for example.

The neurological disease may be associated with aberrant lysosome degradation. Alterations in the lysosome degradation may be present in the neurological disease, such as a neurodegenerative disease. Cathepsin imbalance during aging and age-related diseases may provoke deleterious effects on central nervous system (CNS) neurons and lysosomes may be sites for the unfolding and partial degradation of membrane proteins or their precursors that subsequently become expelled from a cell, or are released from dead cells and accumulate as pathological entities.

A health care professional may diagnose a subject as having a disease associated with motor neuron degeneration by the assessment of one or more symptoms of motor neuron degeneration. To diagnose a neurological disease, a physical exam may be followed by a thorough neurological exam. The neurological exam may assess motor and sensory skills, nerve function, hearing and speech, vision, coordination and balance, mental status, and changes in mood or behavior. Non-limiting symptoms of a disease associated with a neurological disease may be weakness in the arms, legs, feet, or ankles; slurring of speech; difficulty lifting the front part of the foot and toes; hand weakness or clumsiness; muscle paralysis; rigid muscles; involuntary jerking or writing movements (chorea); involuntary, sustained contracture of muscles (dystonia); bradykinesia; loss of automatic movements; impaired posture and balance; lack of flexibility; tingling parts in the body; electric shock sensations that occur with movement of the head; twitching in arm, shoulders, and tongue; difficulty swallowing; difficulty breathing; difficulty chewing; partial or complete loss of vision; double vision; slow or abnormal eye movements; tremor; unsteady gait; fatigue; loss of memory; dizziness; difficulty thinking or concentrating; difficulty reading or writing; misinterpretation of spatial relationships; disorientation; depression; anxiety; difficulty making decisions and judgments; loss of impulse control; difficulty in planning and performing familiar tasks; aggressiveness; irritability; social withdrawal; mood swings; dementia; change in sleeping habits; wandering; and change in appetite.

Tests may be performed to rule diseases and disorders that may have symptoms similar to those of neurological diseases, measure muscle involvement, assess neuron degeneration. Non-limiting examples of tests are electromyography (EMG); nerve conduction velocity study; laboratory tests of blood, urine, or other substances; magnetic resonance imaging (MRI); magnetic resonance spectroscopy; muscle or nerve biopsy; transcranial magnetic stimulation; genetic screening; x-rays; fluoroscopy; angiography; computed tomography (CT); positron emission tomography; cerebrospinal fluid analysis; intrathecal contrast-enhanced CT scan; electroencephalography; electronystagmography; evoked response; polysomnogram; thermography; and ultrasound. A health care professional may also assess the patient's family history of diseases associated with motor neuron degeneration and make a diagnosis in part based on a familial history of neurological diseases. A healthcare professional may diagnose a disease associated with neurological disease in a subject after the presentation of one or more symptoms.

Neurodegenerative diseases result in the progressive destruction of neurons that affects neuronal signaling. For example, a neurodegeneration may be amyotrophic lateral sclerosis, Alzheimer's disease, Huntington's disease, Friedreich's ataxia, Lewy body disease, Parkinson's disease, spinal muscle atrophy, primary lateral sclerosis, progressive muscle atrophy, progressive bulbar palsy, and pseudobulbar palsy.

Diseases associated with motor neuron degeneration may be a condition that results in the progressive destruction of motor neurons that interferes with neuronal signaling to the muscles, leading to muscle weakness and wasting. In healthy individuals, upper motor neurons transmit signals from the brain to lower motor neurons in the brain stem and spinal cord, which then transmit the signal to the muscles to result in voluntary muscle activity. The destruction of upper and lower motor neurons affects activity such as breathing, talking, swallowing, and walking, and overtime these functions can be lost. Examples of motor neuron diseases include, but are not limited to, amyotrophic lateral sclerosis, primary lateral sclerosis, progressive muscle atrophy, progressive bulbar palsy, and pseudobulbar palsy.

Neuronal hyperexcitability may occur when receptors for the excitatory neurotransmitter glutamate (glutamate receptors) such as the NMDA receptor and AMPA receptor are over-activated by excess glutamate or by other compounds or neurotransmitters acting on the glutamate receptors. Excitotoxicity may result from neuronal hyperexcitability. Excitotoxicity is the pathological process by which nerve cells are damaged or killed by excessive stimulation. The excessive stimulation allows high levels of calcium ions (Ca') to enter the cell. Ca' influx into cells activates a number of enzymes, including phospholipases, endonucleases, and proteases such as calpain. These enzymes can damage cell structures such as components of the cytoskeleton, membrane, and DNA.

Neuronal hyperexcitability may be involved in spinal cord injury, stroke, traumatic brain injury, hearing loss (through noise overexposure or ototoxicity), epilepsy, painful neuropathies, attention deficit hyperactivity disorder, autism, central pain syndromes, neurodegenerative diseases, multiple sclerosis, Alzheimer's disease, amyotrophic lateral sclerosis (ALS), Parkinson's disease, frontotemporal dementia, schizophrenia, Rasmussen's encephalitis, Huntington's disease, alcoholism or alcohol withdrawal and especially over-rapid benzodiazepine withdrawal, and also Huntington's disease. Other common conditions that cause excessive glutamate concentrations around neurons are hypoglycemia. Blood sugars are the primary glutamate removal method from inter-synaptic spaces at the NMDA and AMPA receptor site.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. As used herein, an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase or modified nucleobase. A "5-methylcytosine" or "mC" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethylcytosine, xanthine, hypoxanthine, 2-aminoadenine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., Angewandte Chemie, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. The internucleoside linkages may be any described herein. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"PIKFYVE", also known in the art as "phosphatidylinositol-3-phosphate 5-kinase type III" or "PIPKIII", is a FYVE finger-containing phosphoinositide kinase encoded by the PIKFYVE gene. PIKFYVE is a highly evolutionarily conserved lipid kinase and also has protein kinase activity, which regulates endomembrane homeostasis and plays a role in the biogenesis of endosome carrier vesicles from early endosomes. PIKFYVE-mediated conversion of PI3P to PI(3,5)P$_2$ blocks recruitment of the protein EEA1. The recruitment is blocked, because PIP3 is needed to form a platform with RAB5 that enables anchoring of EEA1 to early endosomes. EEA1 then drives fusion with endocytic and other endosomal vesicles.

As used herein a "PIKFYVE disease or disorder" includes lysosomal degradation diseases and disorders mediated by PIKFYVE. For example, the a PIKFYVE disease or disorder includes, but is not limited to, amyloid diseases (such as Alzheimer's disease, Parkinson's disease, Huntington's disease, type 2 diabetes, diabetic amyloidosis and chronic hemodialysis-related amyloid), multiple sclerosis, and an MPS disorder (such as MPS I, MPS II, MPS IIIA, MPS TIM, MPS IIIC, MPS HID, MPS IVA, MPS IVB, MPS VI, MPS VII, or MPS IX). In some embodiments, the diseases are autoimmune disorders (such as multiple sclerosis, rheumatoid arthritis, juvenile chronic arthritis, Ankylosing spondylitis, psoriasis, psoriatic arthritis, adult still disease, Becet syndrome, familial Mediterranean fever, Crohn's disease, leprosy, osteomyelitis, tuberculosis, chronic bronchiectasis, Castleman disease), or CNS disorders (such as spongiform encephalopathies (Creutzfeld-Jakob, Kuru, Mad Cow)). The compositions and methods of the disclosure can be used to treat individuals with lysosomal storage diseases comprising administering to a subject in need of treatment a therapeutically effective amount of a PIKfyve ASO or pharmaceutical composition described herein. In some embodiments, the ASOs and compositions of the disclosure decrease or inhibit the activity of PIKfyve and alters the biogenesis, function or dynamics of the endosomal or lysosomal systems in a way that reduces the abundance of the material abnormally stored in the lysosome in lysosomal storage diseases. In some embodiments, the ASOs and compositions target, decrease or inhibit the activity of PIKfyve thus altering the biogenesis, functions, or dynamics of the endoplasmic reticulum or Golgi apparatus in a way that reduces the abundance of the material abnormally stored in the lysosome in lysosomal storage diseases. In other embodiments, the disease is a neurological disorder.

As used herein, "sugar moiety" means an unmodified sugar moiety or a modified sugar moiety. The superscript prime symbol (') is used to describe the numbering of a sugar in a nucleoside or nucleotide (the nucleobase positions are numbered without the prime). When describing the sugar only, the prime symbol is not used. As used herein, "unmodified sugar moiety" means a 2-OH(H) furanosyl moiety, as found in RNA (an "unmodified RNA sugar moiety"), or a 2-H(H) moiety, as found in DNA (an "unmodified DNA sugar moiety"). Unmodified sugar moieties have one hydrogen at each of the 1, 3, and 4 positions, an oxygen at the 3 position, and two hydrogens at the 5 position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2-substituted sugar moiety. Such modified furanosyl sugar moieties include bicyclic sugars and nonbicyclic sugars.

In certain embodiments, modified sugar moieties are nonbicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2, 4, and/or 5 positions. In certain embodiments one or more non-bridging substituent of non-bicyclic modified sugar moieties is branched. Examples of 2-substituent groups suitable for non-bicyclic modified sugar moieties include but are not limited to: 2-F, 2-OCH$_3$ ("OMe" or "O-methyl"), and 2-O(CH$_2$)$_2$OCH$_3$ ("MOE"). In certain embodiments, 2-substituent groups are selected from among: halo, allyl, amino, azido, SH, CN, OCN, CF$_3$, OCF$_3$, O—C$_{1-10}$ alkoxy, O—C$_{1-10}$ substituted alkoxy, O—C$_{1-10}$ alkyl, O—C$_{1-10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_{1-10}$ alkyl, and the 2-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), and alkyl. Examples of 5-substituent groups suitable for non-bicyclic modified sugar moieties include but are not limited to: 5-methyl (R or S), 5-vinyl, and 5-methoxy. In certain embodiments, non-bicyclic modified sugar moieties comprise more than one non-bridging sugar substituent, for example, 2-F-5-methyl sugar moieties and the like.

In certain embodiments, a 2'-substituted non-bicyclic modified nucleoside comprises a sugar moiety comprising a nonbridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_{1-10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a nonbridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4 and the 2 furanose ring atoms. Examples of such 4 to 2 bridging sugar substituents include but are not limited to: 4-CH$_2$-2, 4-(CH$_2$)$_2$-2, 4-(CH$_2$)$_3$-2, 4-CH$_2$—O-2 ("LNA"), 4-CH$_2$—S-2, 4-(CH$_2$)$_2$—O-2 ("ENA"), 4-CH(CH$_3$)—O-2 (referred to as "constrained ethyl" or "cEt"), 4-CH$_2$—O—CH$_2$-2, 4-CH$_2$—N(R)-2, 4-CH(CH$_2$OCH$_3$)—O-2 ("constrained MOE" or "cMOE") and analogs thereof, 4-C(CH$_3$)(CH$_3$)—O-2 and analogs thereof, 4-CH$_2$—N(OCH$_3$)-2 and analogs thereof, 4-CH$_2$—O—N(CH$_3$)-2, 4-CH$_2$—C(H)(CH$_3$)-2, 4-CH$_2$—C(=CH$_2$)-2 and analogs thereof, 4-C(R$_a$R$_b$)—N(R)—O-2, 4-C(R$_a$R$_b$)—O—N(R)-2, 4-CH$_2$—O—N(R)-2, and 4-CH$_2$—N(R)—O-2, wherein each R, R$_a$, and R$_b$, is, independently, H, a protecting group, or C$_{1-12}$ alkyl.

In certain embodiments, such 4 to 2 bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_{1-12}$ alkyl, substituted C$_{1-12}$ alkyl, C$_{1-12}$ alkenyl, substituted C$_{2-12}$ alkenyl, C$_{2-12}$ alkynyl, substituted C$_{2-12}$ alkynyl, C$_{5-20}$ aryl, substituted C$_{5-20}$ aryl, heterocycle radical, substituted heterocycle radical, heteroaryl, substituted heteroaryl, C$_{5-7}$ alicyclic radical, substituted C$_{5-7}$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_{1-12}$ alkyl, substituted C$_{1-12}$ alkyl, C$_{2-12}$ alkenyl, substituted C$_{2-12}$ alkenyl, C$_{2-12}$ alkynyl, substituted C$_{2-12}$ alkynyl, C$_{5-20}$ aryl, substituted C$_{5-20}$ aryl, acyl (C(=O)—H), substituted acyl, a heterocycle radical, a substituted heterocycle radical, C$_{1-12}$ aminoalkyl, substituted C$_{1-12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. Pat. No. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. In a preferred embodiment, the subject or patient is a human. The subject or patient may be undergoing other forms of treatment. In one embodiment, the patient has a neurological disease due to a mutation in the C9ORF72 gene (for instance, the patient may be haploinsufficient for the C9ORF72 gene (e.g., one which results in a 50% or greater reduction in C9ORF72 protein activity), or the C9ORF72 gene may comprises a GGGGCC repeat expansion (such as a (GGGGCC)$_n$ (SEQ ID NO: 534) hexanucleotide expansion in C90RF72)). The variable "n" can be at least 30.

A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of a receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art.

As used herein, the term "treat" or "treating" a subject, refers to administering a composition or agent described herein to the subject, such that at least one symptom of a disease or disorder is healed, alleviated, relieved, altered, remedied, reduced, ameliorated, or improved. Treating includes administering an amount effective to alleviate, relieve, alter, remedy, reduce, ameliorate, and/or improve one or more symptoms associated with a disease or disorder. The treatment may inhibit deterioration or worsening of a symptom associated with the disease or disorder.

The herein described methods of treatment may comprise administering to a subject in need thereof a composition comprising an effective amount of one or more antisense oligonucleotides that treats neurological diseases by inhibiting or suppressing PIKFYVE expression. The one or more antisense oligonucleotides may decrease or inhibit neurodegeneration. The one or more antisense oligonucleotides may decrease neuronal hyperexcitability. Reducing PIKFYVE mRNA and PIKFYVE protein levels suppresses neurodegeneration driven by toxic TDP-43 aggregates, DPR aggregates (for example, in C9ORF72-ALS patients), and by promoting the retention of TDP-43 in the nucleus. Delivery of the ASOs targeting PIKFYVE mRNA described herein reduces PIKFYVE protein levels.

The composition may inhibit kinase activity by inhibiting expression of a kinase. The composition may inhibit PIKFYVE kinase activity or expression. The one or more antisense oligonucleotides can be combined with small molecule therapeutic agents (such as apilimod and/or YM201636).

The disclosure provides oligonucleotides (modified or unmodified) that can be used to modulate PIKFYVE expression. Table 1 provides (5' to 3') generic sequence of bases for the PIKFYVE antisense oligonucleotides or inhibitory nucleic acids of the disclosure:

TABLE 1

| SEQ ID NO. | Sequence |
| --- | --- |
| 1 | ATGGCATGATCCCCATAAGC |
| 2 | AGGACCAGTACAACCTGTAG |
| 3 | AGGTGCCCCAACTTGTTACC |
| 4 | ACTAAGGTGCCCCAACTTGT |

TABLE 1-continued

| SEQ ID NO. | Sequence |
|---|---|
| 5 | ACCAGGTAGTCCCAAATAAC |
| 6 | GCCTGACCCCTATACTTGAC |
| 7 | CTGACCCCTATACTTGACAG |
| 8 | TTAAGCCCTTTGGTCCAACC |
| 9 | GAGTTAGCACCCTCTACTAC |
| 10 | GTCATAAGTCCTTGGTCAAC |
| 11 | AAGCCTGACCCCTATACTTG |
| 12 | AGCCTGACCCCTATACTTGA |
| 13 | CATCCTATTAGCTTAAACCC |
| 14 | CCTGACCCCTATACTTGACA |
| 15 | TATGATCTGATAGCCAACTC |
| 16 | GTACCAGGACCAGTACAACC |
| 17 | CAGGACCAGTACAACCTGTA |
| 18 | ACACCCTTTGGAGTGTCTAG |
| 19 | GCCCCAACTTGTTACCTAAG |
| 20 | CCCCAATCTAGTTCAAGCAT |
| 21 | TCCAAGAGTTAGCACCCTCT |
| 22 | GGACCAGTACAACCTGTAGT |
| 23 | AAACCCAGTGTAGCTCCATT |
| 24 | TGCCCCAACTTGTTACCTAA |
| 25 | CCAATAGCAAGCAGCCTATA |
| 26 | CTACAATCAAATCCTGGTAG |
| 27 | GACCAAGTTTATGGACCCCA |
| 28 | GTGACCACCATCTATAGTTA |
| 29 | CTAAGGTAACTGTTCCTAGA |
| 30 | TGACCAAGTTTATGGACCCC |
| 31 | ACCAAGTTTATGGACCCCAA |
| 32 | GCAATAAAGCTAACCACATC |
| 33 | GATTCTACCACACAGTACAC |
| 34 | GAGCCCTAACTGTATCTTCC |
| 35 | TAGCTGATTGCCCCTTAACA |
| 36 | GAGACTGCTAAGGCTACTAC |
| 37 | GCTAAGCCCTAAGTATATCC |
| 38 | ACTACTGGTAAGGCAGTCCC |
| 39 | GGTATCCCTACACTTCTACA |
| 40 | GAGTACCAGGACCAGTACAA |
| 41 | ATAACCCCCTGCTAAGAGC |
| 42 | CTTAGCTGATTGCCCCTTAA |
| 43 | GCTATACTACTAGAAGAACC |
| 44 | GTACCTAAATACAGGTCCTA |
| 45 | AGGTATCCCTACACTTCTAC |
| 46 | GCCTACATCCAGTTGATTAG |
| 47 | GAGTGGTAATCAGTCCTATT |
| 48 | GACAAAGTCCTACCTGGTAC |
| 49 | GTAATCTGTTGAGATACACC |
| 50 | TCCTTAATACCCCAGGTTAT |
| 51 | TTCCATAACTAAGGTGCCCC |
| 52 | AACTAAGGTGCCCCAACTTG |
| 53 | GTGCCCCAACTTGTTACCTA |
| 54 | CAAGTCCCTATAACATAACC |
| 55 | GAGCAGTCAGATGTAGTTCC |
| 56 | AAGGATGGTGTAGGTTCCAA |
| 57 | TAACCCACTAGAATAGCACC |
| 58 | GGTATGCCCACCAAAGTTGT |
| 59 | GTACACCTTAGTCTAACAGT |
| 60 | ACCAAGGTACTCTGAACCTA |
| 61 | TGAGTGGTAATCAGTCCTAT |
| 62 | TACCCTTACCTAATCAAGAG |
| 63 | GTGAGCCCTAACTGTATCTT |
| 64 | AATAACCCCCTGCTAAGAG |
| 65 | AACCAATAGTGACTTATGGC |
| 66 | TTAGCTGATTGCCCCTTAAC |
| 67 | AGCTGATTGCCCCTTAACAG |
| 68 | GCTAGTTTACATACCTGTCC |
| 69 | CCTTAATACCCCAGGTTATC |
| 70 | TAACTAAGGTGCCCCAACTT |
| 71 | TAAGGTGCCCCAACTTGTTA |
| 72 | CCCAACTTGTTACCTAAGCA |
| 73 | GTTGGCACATCACACTATTA |
| 74 | ATGTTGAGGCTGTCACACTA |
| 75 | CTAACCTAAGGTAACTGTTC |
| 76 | AGGACTAGAGACCACTTAAC |
| 77 | ACTTAACCTCCCCCTACATC |
| 78 | ATGGTGTAGGTTCCAAACCC |
| 79 | GGATCTACTCCTACTACTCC |
| 80 | TGACCCCTATACTTGACAGA |
| 81 | CCTTTGGTCCAACCTATAAT |
| 82 | GGTAAAACCTGACCTATGTC |

TABLE 1-continued

| SEQ ID NO. | Sequence |
|---|---|
| 83 | AGCCCAATAATGGAGTTGAC |
| 84 | GCCCAATAATGGAGTTGACA |
| 85 | TTACTGGACAGATCCCTTAC |
| 86 | CTGAGTGGTAATCAGTCCTA |
| 87 | AGAGTTAGCACCCTCTACTA |
| 88 | CCAATGCTGGTCAGTTGCTC |
| 89 | ACATAGTCCAATACCCTTAC |
| 90 | ACTGCCATTAGGACTGTTAC |
| 91 | GAAAGTAGTTGGACTCTCCC |
| 92 | TAGTTGGACTCTCCCAGTGC |
| 93 | GCTCCAAGTACTATGTCAAC |
| 94 | GGATAGAGGATTCAAGGCTC |
| 95 | TAACCCCCTGCTAAGAGCC |
| 96 | ACTCAAGAACCAACCTGTAG |
| 97 | TGCTACAACCCAACTCCCCC |
| 98 | GATTGCCCCTTAACAGAACC |
| 99 | GTTTAGACTTGCCACACTAA |
| 100 | TAAGCCCTGTCAGCACAAGG |
| 101 | GGTCTTGTAGACACCAATAA |
| 102 | CTTAATACCCCAGGTTATCT |
| 103 | TTAATACCCCAGGTTATCTC |
| 104 | CATAACTAAGGTGCCCCAAC |
| 105 | AGTGGAGTACTATGGACTAA |
| 106 | GCCCATACTCAAGTTTATCC |
| 107 | CAATGTTGAGGCTGTCACAC |
| 108 | GGCATAGCTTATGGATCAAA |
| 109 | GGCTTTCACTCCACCAGATT |
| 110 | GACCCATCTCTCAGGTGATC |
| 111 | TAGCACAGGTATCCCTACAC |
| 112 | GCCTGTAGCCCTCCCCTAAA |
| 113 | TCCCAGTTGGTAATTCCACC |
| 114 | CCCAGTGGTAATTCCACCC |
| 115 | TGGTAATTCCACCCCTCCAA |
| 116 | GGACTAGAGACCACTTAACC |
| 117 | GACCACTTAACCTCCCCCTA |
| 118 | GAGTACCCTCCAAAGAATTT |
| 119 | ATGGAAGCCTGACCCCTATA |
| 120 | GCCCTGAACTAGATAAACAC |
| 121 | GCCCTTTGGTCCAACCTATA |
| 122 | CCCTTTGGTCCAACCTATAA |
| 123 | GACAGTAAAGGCTCCACCTG |
| 124 | TCAACAAGAAGCCTACTGAC |
| 125 | ATCATAAGAGCCCCAATCAT |
| 126 | CATAAGAGCCCCAATCATCT |
| 127 | TGATCTGATAGCCAACTCAA |
| 128 | TCCTGAGTGGTAATCAGTCC |
| 129 | GACCTACTACAAACTATCAG |
| 130 | AGACCAGGTTCAATAGAATC |
| 131 | AGTACCAGGACCAGTACAAC |
| 132 | AGTCCAATACCCTTACCTAA |
| 133 | GCATGTTAGATCCAAATCCC |
| 134 | GCCCAATAGCAAGCAGCCTA |
| 135 | GACTGACTAAAGGAGGAGCC |
| 136 | CAACCAGTATCAATACCCTC |
| 137 | TGGATAGAGGATTCAAGGCT |
| 138 | GTCCCAGCAAATCAACTACC |
| 139 | GTAGTTACCACCTAAACAGA |
| 140 | GATCACCAGACTCAAGAACC |
| 141 | GCAGCAACCTACCTGACATA |
| 142 | AGCAACCTACCTGACATACC |
| 143 | GCAACCTACCTGACATACCT |
| 144 | GACACCCTTTGGAGTGTCTA |
| 145 | CCTTAGCTGATTGCCCCTTA |
| 146 | TACCATATAGGAAACCTCCT |
| 147 | CTATACTACTAGAAGAACCC |
| 148 | GTGCCCCAAACAAGAAGTT |
| 149 | GTACACAAACATCCCTCTAA |
| 150 | CCATATTACACCTTAGGAAC |
| 151 | CCCCAACTTGTTACCTAAGC |
| 152 | CCAACTTGTTACCTAAGCAC |
| 153 | GCCTAACCAGTGGAGTACTA |
| 154 | ACCAGTGGAGTACTATGGAC |
| 155 | GTATACCATCCACCTGAGTT |
| 156 | GTGGCAAAAGTTCACTACTC |
| 157 | GGTACTCTTCAGATACCTAA |
| 158 | GTACCTGAATCAAGACCCAC |
| 159 | TGGTAAGGCAGTCCCAACAA |
| 160 | ACAGGCATAGCTTATGGATC |

TABLE 1-continued

| SEQ ID NO. | Sequence |
| --- | --- |
| 161 | AGGCATAGCTTATGGATCAA |
| 162 | TAGCACCCTAAACCATCAAT |
| 163 | AGCAAGTAGTTACCCTTGAG |
| 164 | TCCACTATTAAGGATCTTCC |
| 165 | GCTGCCACCTAGAATTAGGT |
| 166 | TTAGCACAGGTATCCCTACA |
| 167 | TAGCCTGTAGCCCTCCCCTA |
| 168 | GTTGGTAATTCCACCCCTCC |
| 169 | CCTACATCCAGTTGATTAGC |
| 170 | GATTCACAGGACTAGAGACC |
| 171 | AGGTGTCCAAACTACCATAA |
| 172 | GTGTCCAAACTACCATAAAC |
| 173 | CCTAACCAGTCAGCTATTAG |
| 174 | GATCCCTTTCCATGTACTAG |
| 175 | GCCTAGCATATATTACCCCA |
| 176 | GGAGACCACTATATTATCCC |
| 177 | GACAACCAGCAGAATCCCTA |
| 178 | GGTACTATATCCAACTGGAC |
| 179 | CATTAGGTATGGCATGATCC |
| 180 | GAACATCACTTAAATGGTCC |
| 181 | AGCCCTTTGGTCCAACCTAT |
| 182 | GTATGCCCACCAAAGTTGTC |
| 183 | ATACCAATGGCAAGGTTTGG |
| 184 | GCAAGTGGCAGCCCAATAAT |
| 185 | GCCAATAATCACACCCTTGG |
| 186 | ACAGATCCCTTACACTATCA |
| 187 | ATCCCATACAGCCAGTTTGG |
| 188 | GCAACCAAGGTACTCTGAAC |
| 189 | TAAGTCCTTGGTCAACTTGC |
| 190 | GATGCCACCTAAATTGCTGG |
| 191 | GGATTCCCAGTTTAAGTCAA |
| 192 | GAAAGGTTATCTGTTGTGCC |
| 193 | GACTCCTTATAGTCACTACC |
| 194 | TACCAGGACCAGTACAACCT |
| 195 | GACCAGTACAACCTGTAGTA |
| 196 | GGTACAAAAGGTTCCAGTAG |
| 197 | GTACAAAAGGTTCCAGTAGC |
| 198 | GCTTCACATAGTCCAATACC |
| 199 | GTCCAATACCCTTACCTAAT |
| 200 | TACCTAATCAAGAGAAGGTC |
| 201 | TGAAAGTAGTTGGACTCTCC |
| 202 | AAAGTAGTTGGACTCTCCCA |
| 203 | ACCTAAGCCCACCTACAATA |
| 204 | ACTAAGTTCAGCTACCACCA |
| 205 | AACCCCCTGCTAAGAGCCA |
| 206 | GCACTGTGGCTATTACACCC |
| 207 | ACCATGATGCTACCCTCAGT |
| 208 | GCCCCTTGAGTGCTGTTTAT |
| 209 | ACCAGGAGCATTTGTTGATC |
| 210 | ATGCTACAACCCAACTCCCC |
| 211 | GCTGATTGCCCCTTAACAGA |
| 212 | GACTGCTAAGGCTACTACAA |
| 213 | GTGAGGATCATGTAACAGTC |
| 214 | AGTTTAGACTTGCCACACTA |
| 215 | GTGTACCTAAATACAGGTCC |
| 216 | TGCCCACTGAAACCTTACTC |
| 217 | TATGCCCATCCCTAAGTTGT |
| 218 | GGACTATCTCTAATCAGTGG |
| 219 | AAGGTGCCCCAACTTGTTAC |
| 220 | TCATTGCCTTACCTAAGTAC |
| 221 | CATTGCCTTACCTAAGTACA |
| 222 | CAGTGGAGTACTATGGACTA |
| 223 | GGAGTACTATGGACTAAGAA |
| 224 | TAAGCCCTAAGTATATCCTC |
| 225 | AAGTTCACTACTCCCAACTA |
| 226 | GGTTGGCACATCACACTATT |
| 227 | GTTTGCTTAACCAATGCTGG |
| 228 | ACAGTTTGCCTAAACCTGGC |
| 229 | ACACAATCCCATGATAGGAC |
| 230 | CCCCCAATCTAGTTCAAGCA |
| 231 | GACTACCTCCTACTTTTAGT |
| 232 | AAGTACCTGAATCAAGACCC |
| 233 | CTACTGGTAAGGCAGTCCCA |
| 234 | GGTAAGGCAGTCCCAACAAA |
| 235 | TTAACAGCAAGTAGTTACCC |
| 236 | TCACACTAACCTAAGGTAAC |
| 237 | GATCTAAGAGTTAAGCTCTC |
| 238 | TAGAATACTTGACCCATCTC |

TABLE 1-continued

| SEQ ID NO. | Sequence |
|---|---|
| 239 | GCAACCCTATGTAAGTCTAT |
| 240 | GGCTGCCACCTAGAATTAGG |
| 241 | GTATCCCTACACTTCTACAC |
| 242 | AACTGTTCCTCCCAGTTGGT |
| 243 | CCAGTTGGTAATTCCACCCC |
| 244 | TTGGTAATTCCACCCCTCCA |
| 245 | GGTCAAAGACCTGAGTCACC |
| 246 | ACTCATGGAGTATTACTGCC |
| 247 | ATGGAGTATTACTGCCCCAA |
| 248 | AACCTCCCCTACATCCTAT |
| 249 | CCCATCACATCAAGTTACAG |
| 250 | TATGACAATCAATCCCACCC |
| 251 | GAAATTCCCCTACCCAGTCC |
| 252 | AATTCCCCTACCCAGTCCTA |
| 253 | CCCTAGACAGTGTAGTAGTT |
| 254 | TTCCAAGAGTTAGCACCCTC |
| 255 | GTATATCCCAATGATACCAG |
| 256 | AACCAGTCAGCTATTAGAAC |
| 257 | GCCCTGCCATCAAAAACTC |
| 258 | TCAGGATCTACTCCTACTAC |
| 259 | CAGGATCTACTCCTACTACT |
| 260 | GAGCCACTTACAGATGATCC |
| 261 | GTTATTAGACACCTACTCTC |
| 262 | CTCTGTAGTAGTTTAGGTGG |
| 263 | GGAAGCCTGACCCCTATACT |
| 264 | GACCCCTATACTTGACAGAA |
| 265 | CTGCCCTGAACTAGATAAAC |
| 266 | GCTAAAACTCCAATCCTATC |
| 267 | CCTATTAGCTTAAACCCATC |
| 268 | ACCATTTGCTAGATAGGTGC |
| 269 | GGCAGCCCAATAATGGAGTT |
| 270 | GCAGCCCAATAATGGAGTTG |
| 271 | ACAACTATGATCTGATAGCC |
| 272 | GGAAGCTAGTTATACAACAC |
| 273 | ATCAGTCCTATTAACCTACC |
| 274 | GGTTAACTTAGCTTGGTCTC |
| 275 | GACAGGATTCCCAGTTTAAG |
| 276 | ACTTGAGTACCAGGACCAGT |
| 277 | CTTCACATAGTCCAATACCC |
| 278 | TTCACATAGTCCAATACCCT |
| 279 | CATAGTCCAATACCCTTACC |
| 280 | TAGTCCAATACCCTTACCTA |
| 281 | GGCTGCTCAATGACAAGTGG |
| 282 | GGACTAACCCAGAGGTCACC |
| 283 | GAGTCTGCCTATTCCTGATC |
| 284 | AGTAGTTGGACTCTCCCAGT |
| 285 | GTTCCTACAGTTTAACACAG |
| 286 | GGTTCCCACCAACAGAATG |
| 287 | TACCTAAGCCCACCTACAAT |
| 288 | ACCAGTATCAATACCCTCAA |
| 289 | GATGATCTCAGCTAGAATCC |
| 290 | GATCTCAGCTAGAATCCTTA |
| 291 | ATGGATAGAGGATTCAAGGC |
| 292 | AGCCCTAACTGTATCTTCCC |
| 293 | CTAAGAGTGATGACAGTTCC |
| 294 | GGACACTTAAACAGGCACTA |
| 295 | GAAAAATAACCCCCCTGCTA |
| 296 | AAAATAACCCCCCTGCTAAG |
| 297 | GACTGACTCCTATCCAACAC |
| 298 | CACCCTATTATACTCAGAGC |
| 299 | GTTTCTAGCCCCTTGAGTGC |
| 300 | GTACCATATAGGAAACCTCC |
| 301 | ACCATATAGGAAACCTCCTC |
| 302 | CAAGTTTAGACTTGCCACAC |
| 303 | CCTGCTGAAGCTATACTACT |
| 304 | TACTAGAAGAACCCATGAGC |
| 305 | GATCCAGGATTATCATACCA |
| 306 | GCTTCACCCTTCTAGGACTA |
| 307 | GATTGCTCCTACCACTCTTG |
| 308 | GGTTACTTCACAAACTCCAA |
| 309 | GCTGACCAAGTTTATGGACC |
| 310 | GGTATTACACACTCAGCCTA |
| 311 | GTATTACACACTCAGCCTAG |
| 312 | GTCTCCTTAATACCCCAGGT |
| 313 | CTTCCATAACTAAGGTGCCC |
| 314 | GGTGCCCCAACTTGTTACCT |
| 315 | CCCCTGTTCTCTAATGTACT |
| 316 | GCACTGCCAAGCTATCAGAT |

TABLE 1-continued

| SEQ ID NO. | Sequence |
|---|---|
| 317 | TGCCAAGCTATCAGATAAGC |
| 318 | CCAGTGGAGTACTATGGACT |
| 319 | CTAATCAATGTGCTAAGCCC |
| 320 | GCACAGAATTAGCCCATACT |
| 321 | GAATTAGCCCATACTCAAGT |
| 322 | CTTAGAAGTCCCCAAGTCTA |
| 323 | CCTCAATAACCATGACAGGT |
| 324 | TCAGGTACTCTTCAGATACC |
| 325 | GCTCTTACATTCACCAGATA |
| 326 | TTGCTTAACCAATGCTGGTG |
| 327 | GCATACAGTTTGCCTAAACC |
| 328 | CACAATCCCATGATAGGACT |
| 329 | CAATCCCATGATAGGACTAT |
| 330 | TGTCAACCTAACAAGTTGGT |
| 331 | GTCAACCTAACAAGTTGGTT |
| 332 | TACTGGTAAGGCAGTCCCAA |
| 333 | CACCAGGTAGTCCCAAATAA |
| 334 | GGTAGTCCCAAATAACTTTC |
| 335 | ATTAGCACAGGTATCCCTAC |
| 336 | GTAGCCCTCCCCTAAATTCT |
| 337 | GGTAATTCCACCCCTCCAAC |
| 338 | GTCAAAGACCTGAGTCACCT |
| 339 | TGTGAGAGATCAACTCAACA |
| 340 | GGAGTATTACTGCCCCAAAA |
| 341 | CTAGAGACCACTTAACCTCC |
| 342 | GAGACCACTTAACCTCCCCC |
| 343 | CCCCCTACATCCTATCACTA |
| 344 | CTATAGTGTATCCAGCCAAT |
| 345 | GGATGGTGTAGGTTCCAAAC |
| 346 | GATGGTGTAGGTTCCAAACC |
| 347 | TGTTACCACATTTCAGTCCC |
| 348 | AACTTCCAAGAGTTAGCACC |
| 349 | AGTACCCTCCAAAGAATTTC |
| 350 | GCCTAACCAGTCAGCTATTA |
| 351 | CCAGTCAGCTATTAGAACTA |
| 352 | GGTTTTGTCAAGCTAACAAC |
| 353 | GGCTGTAATGACCTCCCCTG |
| 354 | CTCAGGATCTACTCCTACTA |
| 355 | AGGATCTACTCCTACTACTC |
| 356 | GAAGCCTGACCCCTATACTT |
| 357 | GTAAAACCTGACCTATGTCC |
| 358 | GCTTAAACCCATCAAACTGA |
| 359 | TCCAAATGGCTGATGTAACC |
| 360 | CAGCCCAATAATGGAGTTGA |
| 361 | GGTCTGTTTACTGGACAGAT |
| 362 | CAGATCCCTTACACTATCAA |
| 363 | ATCCAGACCTTTAGTTACCA |
| 364 | AATCATAAGAGCCCCAATCA |
| 365 | GATCTGATAGCCAACTCAAT |
| 366 | GGATGGCAAGATCCCATACA |
| 367 | GAACCCCAAGAGTGATGACC |
| 368 | CCTGAGTGGTAATCAGTCCT |
| 369 | TAACCTACCTACCCAAAGCC |
| 370 | GCACTAGATGGTTTGAATAC |
| 371 | GATCAGGCTCATTCACAACA |
| 372 | GCCACAAAGTTACCTACTAG |
| 373 | GGAACTTAGCATCACATTAG |
| 374 | GACAGCTCCACAGGTATCAA |
| 375 | GCTATTATTAGACCAGGTTC |
| 376 | GACTTGAGTACCAGGACCAG |
| 377 | TTGAGTACCAGGACCAGTAC |
| 378 | CAGTTCAAGGACTAGCTCTT |
| 379 | CACATAGTCCAATACCCTTA |
| 380 | ATAGTCCAATACCCTTACCT |
| 381 | CTGCCATTAGGACTGTTACA |
| 382 | TGCCATTAGGACTGTTACAG |
| 383 | AAGGCTCACCTATAAACAAC |
| 384 | GTATGACCATCCTTACATAC |
| 385 | AAGTAGTTGGACTCTCCCAG |
| 386 | AGTTGGACTCTCCCAGTGCC |
| 387 | GTACAGGTCACTACAGATGA |
| 388 | TAATATCCACTCCTACCTGG |
| 389 | CCTACCTAAGCCCACCTACA |
| 390 | GTGTAGCTCCATTTCAACTT |
| 391 | GGTGCTACTTACTGAACACC |
| 392 | CCCTAACTGTATCTTCCCAA |
| 393 | CACTGGCTAGTGCTTTATCC |
| 394 | GCAACTGTCAACCAAGACTG |

TABLE 1-continued

| SEQ ID NO. | Sequence |
|---|---|
| 395 | GTAATCCAGGTCATAGTTCC |
| 396 | CCAATAGTGACTTATGGCAT |
| 397 | CCAGGCAGCAACCTACCTGA |
| 398 | GGAGACTGCTAAGGCTACTA |
| 399 | AGACTGCTAAGGCTACTACA |
| 400 | GCATTACCAATAAATCCACC |
| 401 | TGGTCAGTCTACCCAGTTAA |
| 402 | GCCCTTCTCACATTAAGCAT |
| 403 | AATTACCATGCCCCAGAGAC |
| 404 | CCTAAATACAGGTCCTAATG |
| 405 | AACATCAATCTGAGACACCC |
| 406 | GTTGCCTATCCTCACTTACC |
| 407 | CCTCAGGTCAATCTATGCTA |
| 408 | TATGCCCACTGAAACCTTAC |
| 409 | AGGTTACTTCACAAACTCCA |
| 410 | GCCCATATTACACCTTAGGA |
| 411 | ATAACTAAGGTGCCCCAACT |
| 412 | ATCTTCCACTAAGAAGTCCC |
| 413 | TGCTAAGCCCTAAGTATATC |
| 414 | AAGCCCTAAGTATATCCTCA |
| 415 | GTATCTATATGAGACTCCAG |
| 416 | TATACCATCCACCTGAGTTC |
| 417 | GCAAAGTTCACTACTCCCA |
| 418 | GTTCACTACTCCCAACTACT |
| 419 | AGGTACTCTTCAGATACCTA |
| 420 | GTCCCTATAACATAACCTAG |
| 421 | CAAGTGACCACCATCTATAG |
| 422 | GCTAGTCAAGTCTCATTAAC |
| 423 | TTACACAATCCCATGATAGG |
| 424 | ACAATCCCATGATAGGACTA |
| 425 | CCCAATCTAGTTCAAGCATC |
| 426 | AGATGGTGACTACCTCCTAC |
| 427 | CTGGTAAGGCAGTCCCAACA |
| 428 | TAAGGCAGTCCCAACAAAAC |
| 429 | AAGCAGGACCTGTCTGTTAC |
| 430 | GACAGGCATAGCTTATGGAT |
| 431 | CTAGATTAGTGAACAGTAGC |
| 432 | CACACTAACCTAAGGTAACT |
| 433 | CCAGGTAGTCCCAAATAACT |
| 434 | GTAGTCCCAAATAACTTTCC |
| 435 | ATTGCCCCCAGACTCCTACT |
| 436 | CCCCAGACTCCTACTTAAAC |
| 437 | GAGTATAGAATACTTGACCC |
| 438 | GTAAATTAGCACAGGTATCC |
| 439 | ACTGTTCCTCCCAGTTGGTA |
| 440 | GTTCCTCCCAGTTGGTAATT |
| 441 | CTCCCAGTTGGTAATTCCAC |
| 442 | CAGTTGGTAATTCCACCCCT |
| 443 | AGTTGGTAATTCCACCCCTC |
| 444 | GTACCCTGATGATACCCTTC |
| 445 | GGTTAGAATGGATCAAAACC |
| 446 | GTCAAAGTAGGTCCACTGAA |
| 447 | ACTTCCAAGAGTTAGCACCC |
| 448 | ACCCTCTACTACCAAGCAGT |
| 449 | GGTGTCCAAACTACCATAAA |
| 450 | CTAACCAGTCAGCTATTAGA |
| 451 | ATCAGCAAGAGCCTATTAAG |
| 452 | GCAGGTTCAGTGCTAAGATT |
| 453 | GTAAGACTTGCTGACTCACC |
| 454 | CAAGTAGCTGTAAGTCCAAC |
| 455 | ATCCCCAAAGAGACCTATGC |
| 456 | CAACCAGCAGAATCCCTATA |
| 457 | TTAGGTATGGCATGATCCCC |
| 458 | TAAGCCCTTTGGTCCAACCT |
| 459 | AAGCCCTTTGGTCCAACCTA |
| 460 | TACCAATGGCAAGGTTTGGC |
| 461 | TTGTTCTGGCTGACCAAGTC |
| 462 | GTTCTGGCTGACCAAGTCTG |
| 463 | TCACCTTGACTTAGGCAAAC |
| 464 | GGCAAACCACTCCAAGTTGA |
| 465 | CAAGTGGCAGCCCAATAATG |
| 466 | TTTACTGGACAGATCCCTTA |
| 467 | TACTGGACAGATCCCTTACA |
| 468 | GGACAGATCCCTTACACTAT |
| 469 | CTGAACAGAGTACTAACCAC |
| 470 | ATAAGAGCCCCAATCATCTA |
| 471 | CCTAAACACATGAACCTGGT |
| 472 | TAATGTAGACTGGTCCAGGC |

TABLE 1-continued

| SEQ ID NO. | Sequence |
|---|---|
| 473 | AAGGAGCCCCCAGTTGATCT |
| 474 | GATCCCATACAGCCAGTTTG |
| 475 | TTGAGGCAACCAAGGTACTC |
| 476 | CAACCAAGGTACTCTGAACC |
| 477 | CCAAGGTACTCTGAACCTAA |
| 478 | AGTAGAACTGTCACTATACC |
| 479 | GTAACAACCACCCCTGGAAA |
| 480 | TTCCTGAGTGGTAATCAGTC |
| 481 | GACTACCTCTATTGTCAACA |
| 482 | ACACCTTGTACTTCAAGTGC |
| 483 | CTTAGTAGTCAGAACTAGCC |
| 484 | GGACAGTCTAAACAGCCACA |
| 485 | GGAAAGGTTATCTGTTGTGC |
| 486 | AAGGTTATCTGTTGTGCCAC |
| 487 | GGACAAAGTCCTACCTGGTA |
| 488 | TGAGTACCAGGACCAGTACA |
| 489 | ACCCTTACCTAATCAAGAGA |
| 490 | TAAAGGAAGCATCCCCTTGT |
| 491 | AACTGCCATTAGGACTGTTA |
| 492 | TGAGAAAGGCTCACCTATAA |
| 493 | ATCTATGCCTTCCAAGGATC |
| 494 | GCTACAGCCCAATAGCAAGC |
| 495 | GGTCATCAGAGTCTGCCTAT |
| 496 | CCTGATCTAAACCCATACCC |
| 497 | GTAGTTGGACTCTCCCAGTG |
| 498 | ACAGACACTAGTATTGCCTC |
| 499 | AATATCCACTCCTACCTGGT |
| 500 | TGGTTCCCCACCAACAGAAT |

In one embodiment, the disclosure provides modified oligonucleotides consisting of 12-30 linked nucleosides and having a nucleobase sequence comprising at least 8, at least 9, at least 10, at least 11 at least 12, at least 13, at least 14, at least 15, at least 16, at least 17, at least 18, at least 19 or at least 20 consecutive nucleotide bases of any of the nucleobase sequences of SEQ ID NO:1-500 in Table 1. In some embodiments, the modified oligonucleotide is at least 80% to 100% (i.e., 80%, 82%, 84%, 86%, 88%, 90%, 92%, 94%, 96%, 98% or 100%; or any numerical range or value between any of the foregoing values) identical to any of the sequences comprising or consisting of SEQ ID NO:1-500.

The sequences provided in Table 1 can be used to design antisense molecules for inhibition of PIKFYVE expression. For example, gapmer oligonucleotides can be designed using the sequences in Table 1 and can comprise a 5'-wing of about 3-5 nucleotides, a 3'-wing of about 3-5 nucleotides and a gap region comprising 8-12 consecutive deoxyribonucleosides of any one of the sequences of Table 1. In one embodiment, an oligonucleotide of the disclosure comprises a gapmer having a gap segment of at least 8, at least 9, at least 10, at least 11 at least 12, at least 13, at least 14, at least 15, at least 16, at least 17, at least 18, at least 19 or at least 20 consecutive nucleotide bases of any of the nucleobase sequences of SEQ ID NO:1-136 in Table 1; flanked by a 5' and 3' wing segments, wherein the gap segment is located between the 5' and 3' wing segments and wherein each of the wing segments comprises a modified sugar. In one embodiment, the gap segment is 8-10 nucleosides in length and each wing segment is 3-5 modified nucleosides in length. In yet another embodiment, an oligonucleotide of the disclosure comprises a 5' wing segment comprising modified sugars and having the nucleobase sequence of the first 3-5 nucleobases of any of SEQ ID NO:1-500, followed by a gap of the next 8-12 unmodified nucleotides of the same sequence corresponding to SEQ ID NO:1-500, followed by a 3' wing segment comprising modified sugars and having the nucleobase sequence of the last 3-5 nucleobases of the same sequence corresponding to SEQ ID NO:1-500. Table 2 provides MOE gapmers of the disclosure.

The 5' and/or 3' wings can comprise the following chemistries: 2'-OMe, 2'-MOE, LNA or DNA, by themselves or used in combination with one another. The backbone linkage of the 5' and/or 3' wings can be phosphorothioate or a mixture of phosphodiester and phosphorothioate. Linkages in the gap region can be phosphorothioate.

In some embodiments, the oligonucleotide is single stranded. In some embodiments the oligonucleotide comprises or is complexed with a moiety that neutralizes charge on the oligonucleotide to promote uptake and transfer across a cell membrane.

In one embodiment, each of the ASOs in Table 1 has the following 5-10-5 motif: 2MOE*2MOE-2MOE-2MOE-2MOE-N*N*N*N*N*N*N*N*N*N*2MOE-2MOE-2MOE*2MOE*2MOE where (i) 2MOE is a nucleobase with a 2'-OCH$_2$CH$_2$—OCH$_3$ group (i.e., 2'-MOE), (ii) N is a nucleobase, (iii) the asterisk (*) refers to a phosphorothioate linkage, and (iv) the dash (-) refers to a phosphodiester linkage. Table 2 below shows this motif on SEQ ID NO: 1-33 (here SEQ ID NO: 501-533).

Table 2: The Sequence of Bases in PIKFYVE Antisense Oligonucleotides—(ASOs). (Gapmer design: 5'-five 2'-methoxyethylribose nucleotides—ten DNA nucleotides—five 2'-methoxyethylribose nucleotides—3'; Capital letters are 2'-methoxyethylribose nucleosides; lower case are DNA nucleosides; asterisks (*) are phosphorothioate linkages; linkages which do not have an asterisk are phosphodiester linkages) (Note that the following table provides 2'MOE wings; however, alternative wings comprising 2'-OMe or LNA (locked nucleic acid) are contemplated).

TABLE 2

| SEQ ID NO. | Sequence |
|---|---|
| 501 | A*TGGCa*t*g*a*t*c*c*c*a*TAA*G*C |
| 502 | A*GGACc*a*g*t*a*c*a*a*c*c*TGT*A*G |
| 503 | A*GGTGc*c*c*c*a*a*c*t*t*g*TTA*C*C |
| 504 | A*CTAAg*g*t*g*c*c*c*c*a*a*CTT*G*T |
| 505 | A*CCAGg*t*a*g*t*c*c*c*a*a*ATA*A*C |
| 506 | G*CCTGa*c*c*c*c*t*a*t*a*c*TTG*A*C |

TABLE 2-continued

| SEQ ID NO. | Sequence |
|---|---|
| 507 | C*TGACc*c*c*t*a*t*a*c*t*t*GAC*A*G |
| 508 | T*TAAGc*c*c*t*t*t*g*g*t*c*CAA*C*C |
| 509 | G*AGTTa*g*c*a*c*c*c*t*c*t*ACT*A*C |
| 510 | G*TCATa*a*g*t*c*c*t*t*g*g*TCA*A*C |
| 511 | A*AGCCt*g*a*c*c*c*t*a*t*ACT*T*G |
| 512 | A*GCCTg*a*c*c*c*t*a*t*a*CTT*G*A |
| 513 | C*ATCCt*a*t*t*a*g*c*t*t*a*AAC*C*C |
| 514 | C*CTGAc*c*c*t*a*t*a*c*t*TGA*C*A |
| 515 | T*ATGAt*c*t*g*a*t*a*g*c*c*AAC*I*C |
| 516 | G*TACCa*g*g*a*c*c*a*g*t*a*CAA*C*C |
| 517 | C*AGGAc*c*a*g*t*a*c*a*a*c*CTG*T*A |
| 518 | A*CACCc*t*t*t*g*g*a*g*t*g*TCI*A*G |
| 519 | G*CCCCa*a*c*t*t*g*t*t*a*c*CTA*A*G |
| 520 | C*CCCAa*t*c*t*a*g*t*t*c*a*AGC*A*T |
| 521 | T*CCAAg*a*g*t*t*a*g*c*a*c*CCI*C*T |
| 522 | G*GACCa*g*t*a*c*a*a*c*c*t*GTA*G*T |
| 523 | A*AACCc*a*g*t*g*t*a*g*c*t*CCA*T*T |
| 524 | T*GCCCc*a*a*c*t*t*g*t*t*a*CCT*A*A |
| 525 | C*CAATa*g*c*a*a*g*c*a*g*c*CTA*T*A |
| 526 | C*TACAa*t*c*a*a*a*t*c*c*t*GGT*A*G |
| 527 | G*ACCAa*g*t*t*t*a*t*g*g*a*CCC*C*A |
| 528 | G*TGACc*a*c*c*a*t*c*t*a*t*AGT*T*A |
| 529 | C*TAAGg*t*a*a*c*t*g*t*t*c*CTA*G*A |
| 530 | T*GACCa*a*g*t*t*t*a*t*g*g*ACC*C*C |
| 531 | A*CCAAg*t*t*t*a*t*g*g*a*c*CCC*A*A |
| 532 | G*CAATa*a*a*g*c*t*a*a*c*c*ACA*T*C |
| 533 | G*ATTCt*a*c*c*a*c*a*c*a*g*TAC*A*C |

The PIKFYVE kinase antisense or inhibitory nucleic acids of the disclosure can inhibit the expression and thus the activity associate with PIKFYVE. The PIKFYVE kinase antisense or inhibitory nucleic acids can include any combination of the oligonucleotides set forth in Table 2 and sequences that are 98%-99% identical thereto.

The PIKFYVE ASOs described herein, such as SEQ ID NO:501-533, suppress PIKFYVE mRNA expression with minimal off-target binding.

Methods of treatment may include any number of modes of administering a disclosed composition. Modes of administration may include aqueous, lipid, oily or other solutions, solutions in simulated cerebrospinal fluid, emulsions such as oil-in-water emulsions, liposomes, aqueous or oily suspensions and the like. Typically, an ASO of the disclosure will be administered directly to the CNS of the subject. Accordingly, the formulation or composition will be sterile and more preferably be suitable for injection. The following formulations and methods are merely exemplary and are in no way limiting.

Formulations suitable for parenteral administration include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored as liquids or in a freeze-dried (lyophilized) condition requiring only the addition of the sterile liquid excipient, for example, water for injections, immediately prior to use. Extemporaneous injection solutions and suspensions may be prepared from sterile powders, granules, and tablets. The formulation may be provided in a pre-filled syringe.

Additional therapeutic agent(s) may be administered simultaneously or sequentially with the disclosed one or more antisense or inhibitory nucleic acids and compositions. Sequential administration includes administration before or after the disclosed one or more antisense or inhibitory nucleic acids or compositions. In some embodiments, the additional therapeutic agent or agents may be administered in the same composition as the disclosed one or more antisense or inhibitory nucleic acids. In other embodiments, there may be an interval of time between administration of the additional therapeutic agent and the disclosed one or more antisense or inhibitory nucleic acids. In some embodiments, administration of an additional therapeutic agent with a disclosed one or more antisense or inhibitory nucleic acids may allow lower doses of the other therapeutic agents and/or administration at less frequent intervals. When used in combination with one or more other active ingredients, the one or more antisense or inhibitory nucleic acids of the disclosure and the other active ingredients may be used in lower doses than when each is used singly. Accordingly, the pharmaceutical compositions of the disclosure include those that contain one or more other active ingredients, in addition to one or more antisense or inhibitory nucleic acids of the disclosure. The above combinations include combinations of one or more antisense or inhibitory nucleic acids of the disclosure not only with one other active compound, but also with two or more other active compounds. For example, the compound of the disclosure may be combined with a variety of drugs to treat neurological diseases. The antisense oligonucleotide may be covalently linked to another oligonucleotide, such as one with a target other than PIKFYVE. The antisense oligonucleotide may be covalently linked to an antibody.

The disclosed one or more antisense or inhibitory nucleic acids can be combined with the following, but are not limited, anticholinergic drugs, anticonvulsants, antidepressants, benzodiazepines, decongestants, muscle relaxants, pain medications, and/or stimulants. Additional types of therapy and treatment include, but are not limited to digital communication devices, feeding tubes, mechanical ventilation, nutritional support, deep brain stimulation, occupational therapy, physical therapy, and/or speech therapy.

The disclosed composition(s) may be incorporated into a pharmaceutical composition suitable for administration to a subject (such as a patient, which may be a human or non-human). The pharmaceutical compositions may comprise a carrier (e.g., a pharmaceutically acceptable carrier). Any suitable carrier can be used within the context of the disclosure, and such carriers are well known in the art. The choice of carrier will be determined, in part, by the particular use of the composition (e.g., administration to an animal) and the particular method used to administer the composition. Accordingly, there is a wide variety of suitable formulations of the composition of the present invention.

The pharmaceutical compositions may include a therapeutically effective amount or a prophylactically effective amount of the antisense oligonucleotide. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of one or more antisense or inhibitory nucleic acids of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical compositions may include one or more pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogenfree water; isotonic saline; Ringer's solution; ethyl alcohol, and phosphate buffer solutions, as well as other non-toxic compatible lubricants such as, but not limited to, sodium lauryl sulfate and magnesium stearate, as well as releasing agents, coating agents, preservatives and antioxidants may also be present in the composition, according to the judgment of the formulator.

The route by which the disclosed one or more antisense or inhibitory nucleic acids are administered, and the form of the composition will dictate the type of carrier to be used.

The pharmaceutical compositions of the disclosure can be administered in a number of ways depending upon whether local or systemic treatment is desired and upon the area to be treated. Administration can be parenteral including intravenous, intraarterial, subcutaneous, intraperitoneal or intramuscular injection or infusion; or intracranial, e.g., intrathecal, intracerebroventricular, or intraventricular, administration. In one embodiment the antisense or inhibitory nucleic acid is administered by intravenous, intraperitoneal, or as a bolus injection or administered directly into the target organ. In another embodiment, the antisense or inhibitory nucleic acid is administered intrathecally or intra-cerebroventricular as a bolus injection.

Carriers for systemic administration typically include at least one of solvent, diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of Theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds and other pharmaceutically acceptable carriers or excipients. For example, an intrathecal cerebrospinal fluid (CSF) catheter can be used to deliver antisense formulations of the disclosure. The catheter can be inserted at the L3 or L4 vertebrae. The distal tip of the catheter extends within the intrathecal space to approximately the L1 vertebrae. Antisense oligonucleotides are dissolved in saline, are sterilized by filtration, and are administered at 0.33 ml/min in a 1.0 ml volume followed by a 0.5 ml sterile water flush. Total infusion time is 4.5 min.

Compositions for parenteral administration typically include 0.1% to 10% of actives and 90% to 99.9% of a carrier including a diluent and a solvent.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

In vivo testing of candidate antisense or inhibitory nucleic acids may be conducted by means known to one of ordinary skill in the art. For example, the candidate one or more antisense or inhibitory nucleic acids may be administered to a mammal, such as a mouse or a rabbit. The mammal may be administered, by any route deemed appropriate, a dose of a candidate antisense or inhibitory nucleic acids. Conventional methods and criteria can then be used to monitor animals for signs of reduction or improvement of motor neuron activity and/or expression or activity of PIKFYVE gene or protein, respectively. If needed, the results obtained in the presence of the candidate antisense or inhibitory nucleic acids can be compared with results in control animals that are not treated with the candidate antisense or inhibitory nucleic acids. Dosing studies may be performed in, or in conjunction with, the herein described methods for identifying one or more antisense or inhibitory nucleic acids capable of treating a neurological disease and/or any follow-on testing of candidate antisense or inhibitory nucleic acids in vivo. One of skill in the art of medicine may determine the appropriate dosage of one or more antisense or inhibitory nucleic acids. The dosage may be determined by monitoring the subject for signs of disease inhibition or amelioration. The dosage may be increased or decreased to obtain the desired frequency of treatment. The toxicity and efficacy of one or more antisense or inhibitory nucleic acids may be determined by standard pharmaceutical procedures in cell cultures or experimental animals, e.g. determining the lethal dose to 50% of the population (LD50) and the dose therapeutically effective in 50% of the population (ED50). The dose ratio of LD50/ED50 is the therapeutic index and, indicating the ratio between the toxic and therapeutic effects. A delivery system may be designed to help prevent toxic side effects, by delivering the one or more antisense or inhibitory nucleic acids to specific targets, e.g., delivered specifically to motor or central nervous system neurons. The optimal dose of the one or more antisense or inhibitory nucleic acids may be determined based on results of clinical electrophysiology or electromyography to analyze excitability in peripheral nerves, for example.

The dosage for use in humans may be determined by evaluating data obtained from animal studies and cell culture assays. The preferred dosage will have little or no toxicity and include the ED50. The dosage may vary depending on the dosage form and route of administration. For any antisense or inhibitory nucleic acid used in the methods described herein, the dosage may be estimated initially in cell culture. A dose may be formulated in animal models that includes the concentration of the test compound which achieves a half maximal inhibition of symptoms (LD50) as determined in cell culture. Such information obtained from cell cultures and animal models may be used to more accurately determine useful doses in humans.

The present invention has multiple aspects, illustrated by the following non-limiting examples.

EXAMPLES

Small molecule inhibitors of PIKFYVE kinase and antisense oligonucleotides (ASOs) that suppress PIKFYVE expression can prevent the degeneration of human and mouse neurons that carry a mutation in the C9ORF72 gene that leads to amyotrophic lateral sclerosis (ALS) and frontotemporal dementia (FTD).

ASOs are an attractive therapeutic option for neurodegenerative diseases because of their ease of delivery to the central nervous system and their relatively low exposure to the periphery. These properties maximize target engagement in the central nervous system and minimize undesired target engagement or off-target effects in the periphery.

The disclosure provides novel antisense oligonucleotide (ASO) sequences targeting the PIKFYVE gene that can suppress PIKFYVE expression in human cells. PIKFYVE ASOs can also rescue the survival of motor neurons derived from sporadic ALS patients. Moreover, PIKFYVE ASOs can lower levels of neurotoxic dipeptide repeat protein aggregates derived from the C9ORF72 repeat expansion in vivo in mice.

Example 1

To identify ASO sequences that suppress PIKFYVE expression in human cells, ASOs were designed (see, Table 2) and synthesized as MOE gapmers, which contains sugar and linkage modifications that increase nuclease resistance and melting temperature while maintaining the ability to be used as a substrate of RNase H. The ability of each ASO to suppress PIKFYVE RNA levels was tested by transfecting them into human embryonic kidney 293T cells with Lipofectamine 2000 at a concentration of 100 nM and measuring PIKFYVE expression 7 days after transfection. As a control, NCASO was used. The relative PIKFYVE expression shown is an average of three technical replicates and values were calculated by normalizing to a GAPDH control. Together, these results, as shown in FIG. 1, show that several PIKFYVE ASOs (SEQ ID NO: 1-33, which correspond to ASO 1-33 in the figure) suppress PIKFYVE expression in human cells.

Example 2

Suppression of off-target genes, such as CNTN5, was predicted in silico for various ASOs described herein. The results are provided in Table 3 below.

TABLE 3

| ASO | (−) strand complementary binding gene | (+) strand complementary binding gene | Total complementary binding gene | Total intron | Total exon |
|---|---|---|---|---|---|
| Tofersen | 11 | 14 | 25 | 23 | 2 |
| Other PIKFYVE ASO #1 | 11 | 11 | 22 | 22 | 0 |
| Other PIKFYVE ASO #2 | 15 | 14 | 29 | 29 | 0 |
| ASO-2 (SEQ ID NO: 2) | 0 | 3 | 3 | 3 | 0 |
| ASO-4 (SEQ ID NO: 4) | 3 | 4 | 7 | 6 | 1 |
| ASO-13 (SEQ ID NO: 13) | 0 | 2 | 2 | 2 | 0 |
| ASO-20 (SEQ ID NO: 20) | 2 | 3 | 5 | 5 | 0 |
| ASO-21 (SEQ ID NO: 21) | 1 | 4 | 5 | 4 | 1 |
| ASO-26 (SEQ ID NO: 26) | 0 | 3 | 3 | 3 | 0 |
| ASO-27 (SEQ ID NO: 27) | 1 | 2 | 3 | 2 | 1 |
| ASO-29 (SEQ ID NO: 29) | 1 | 11 | 12 | 12 | 0 |
| ASO-105 (SEQ ID NO: 105) | 1 | 5 | 6 | 6 | 0 |

Five (5) off-target gene candidates were predicted for ASO-520 (SEQ ID NO:520) from sequence analysis (as compared to 25 for tofersen). Two of these genes have very low expression in the brain and are not detectable in induced neurons. To assess actual off-target suppression for the remaining three genes (ZNF385D, ERC2, and AKAP6), the effect of ASO-520 treatment on the expression of these three genes and PIKFYVE was tested in a patient induced neuron line by qPCR. ASO-520 did not significantly affect their expression at doses that reduced PIKFYVE by 50%.

Example 3

Figure 2:
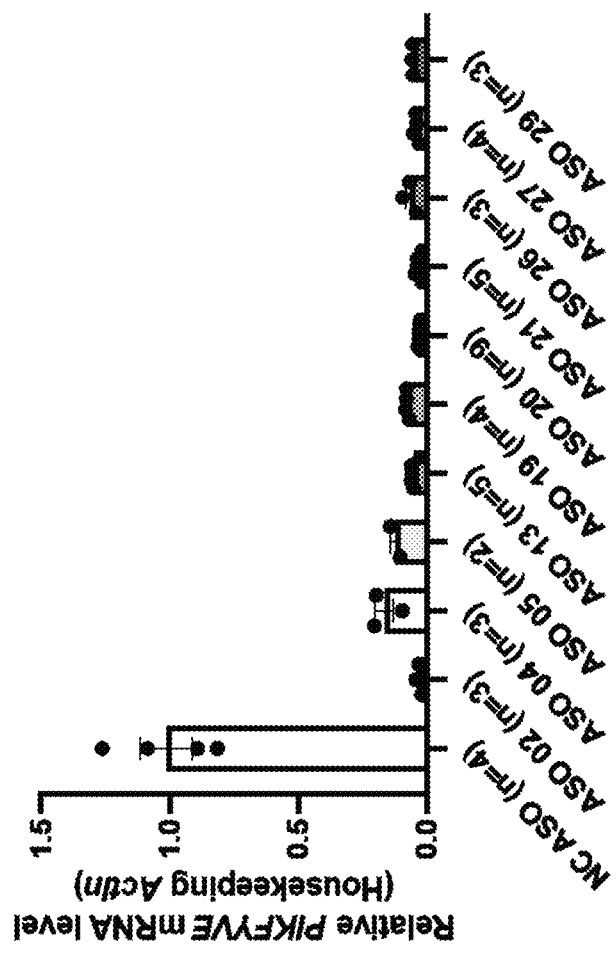
FIG. 2 is a bar graph showing the suppressive effect of various PIKFYVE ASOs in neonate transgenic hPIKFYVE BAC mice.

In the study, neonate transgenic hPIKFYVE BAC mice received 25 µg of negative control ASO or test compound by intracerebroventricular (ICV) injection at P1 (postnatal day 1) and tissue samples were collected 14 days post-treatment. As illustrated in FIG. 2, the ASOs tested were potent PIKFYVE suppressors. At dosages from 0.0004 µg to 25 µg of ASO-520, a dose-dependent PIKFYVE mRNA level reduction was observed in the mice.

Example 4

A TDP-43 mouse model that develops neurodegeneration, motor impairment, and paralysis was used to assess efficacy of PIKFYVE supression. Wils et al., "TDP-43 Transgenic Mice Develop Spastic Paralysis and Neuronal Inclusions Characteristic of ALS and Frontotemporal Lobar Degeneration." PNAS 107(8):3858-63, 2010.

The mice were further genetically modified to delete one coy of PIKFYVE. This deletion significantly rescued motor function in TDP-43 mice, extended mean survival by 28% and reduced the risk of death (hR: hazard ratio) by 73%. The deletion did not cause any motor, cognitive, or health problems in wild-type (WT) mice.

Intracerebroventricular injection of 25 µg of a mPIKFYVE-targeting ASO at postnatal day 1 (5 µg/µl concentration in the central nervous system) significantly decreased PIKFYVE expression by ~50% compared to a negative control (NC) ASO. This PIKFYVE ASO treatment significantly rescued motor function and survival in TDP-43 mice at levels similar to that of the genetic deletion, and did not alter function in WT mice. A 5-fold lower dose of 5 µg of PIKFYVE ASO also significantly rescued motor function and survival at levels similar to the genetic deletion. This established that the ASO has at least a 5-fold therapeutic window in this model.

Histological analysis showed that the number of pathological pTDP-43 aggregates, elevated in the TDP-43 mouse, are significantly lowered with mPIKFYVE ASO treatment and completely rescued to the level of WT mice. Total TDP-43 localization, pathologically localized to the cytoplasm in the TDP-43 mouse, is significantly re-localized to the nucleus upon treatment. The number of motor neurons in the lateral motor column of the spinal cord ventral horn area was fully rescued to the level of WT in the PIKFYVE ASO treated mice.

Example 5

Figure 3:
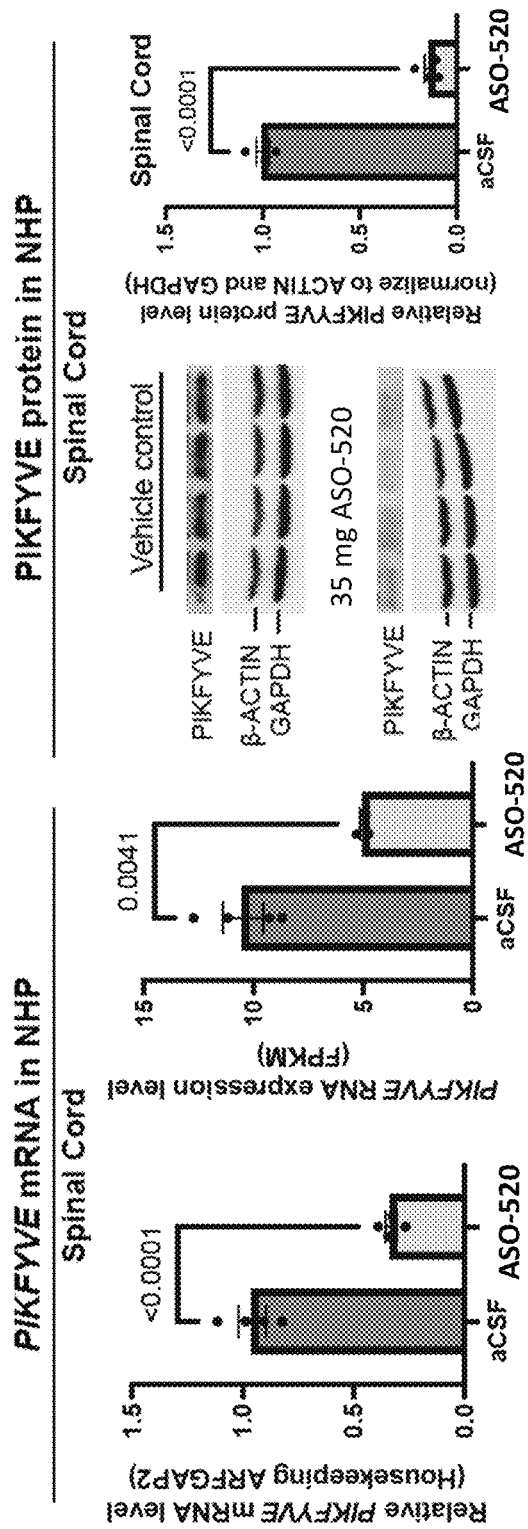
FIG. 3 are bar graphs showing the change in PIKFYVE mRNA and PIKFYVE protein in non-human primates (NHP) with and without treatment of ASO-520 or artificial cerebrospinal fluid (aCSF).

35 mg of ASO-520 was administered intrathecally to non-human primates every other week for two weeks (2 doses). This resulted in reduction in PIKFYVE mRNA and 80% suppression of PIKFYVE, as shown by FIG. 3, with no observed adverse events (including in brain and spinal cord histopathology). (One outlier was removed from the RNA-seq data.)

Example 6

Figure 4B:
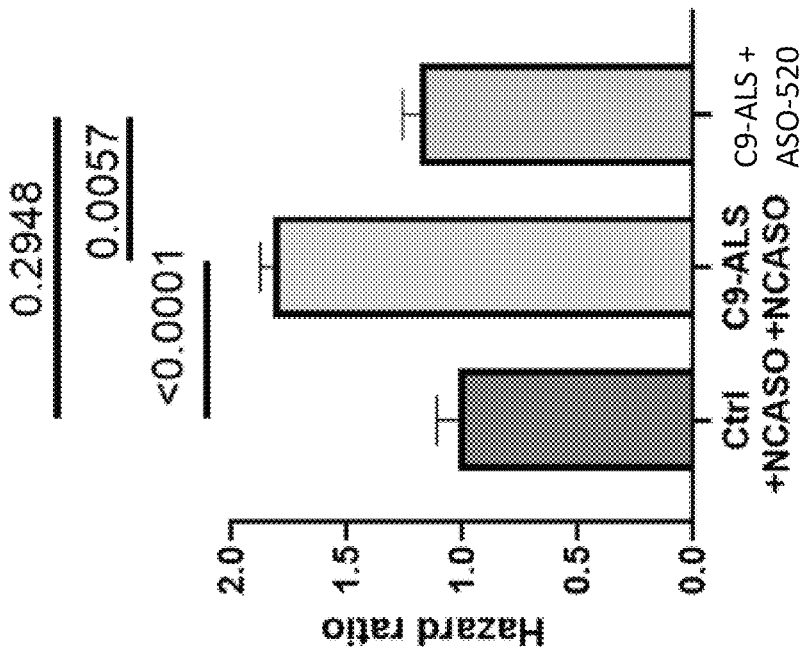
FIG. 4B is a bar graph showing the hazard ratio for control motor neurons in the presence of a NC ASO or C9ALS patient-derived motor neurons in the presence of (i) a NC ASO or (ii) AS-520 (SEQ ID NO: 520).
Figure 4A:
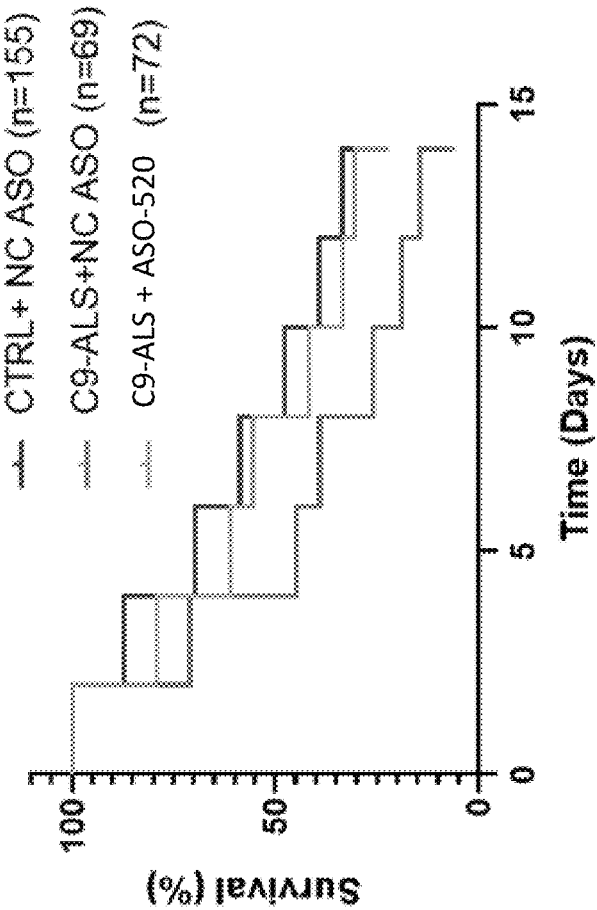
FIG. 4A is a graph showing the percent survival of control motor neurons in the presence of a non-coding ASO (NC ASO) or C9ALS patient-derived motor neurons in the presence of (i) a NC ASO or (ii) AS-20 (SEQ ID NO: 20).

The ability of motor neurons to survive in the presence of a non-coding ASO or AS-520 (SEQ ID NO: 520) was determined. FIG. 4A shows the percent survival of control motor neurons in the presence of a non-coding ASO (NC ASO) or C9ALS patient-derived motor neurons in the presence of (i) a NC ASO or (ii) AS-520. A greater number of C9ALS patient-derived motor neurons survived in the presence of ASO-520 than in the presence of NC ASO. FIG. 4B shows the hazard ratio for control motor neurons in the presence of a NC ASO or C9ALS patient-derived motor neurons in the presence of (i) a NC ASO or (ii) AS-520 (SEQ ID NO: 520). The hazard ratio of C9ALS patient-derived motor neurons in the presence of AS-20 was significantly lower than in the presence of NC ASO.

Figures 5A, 5B:
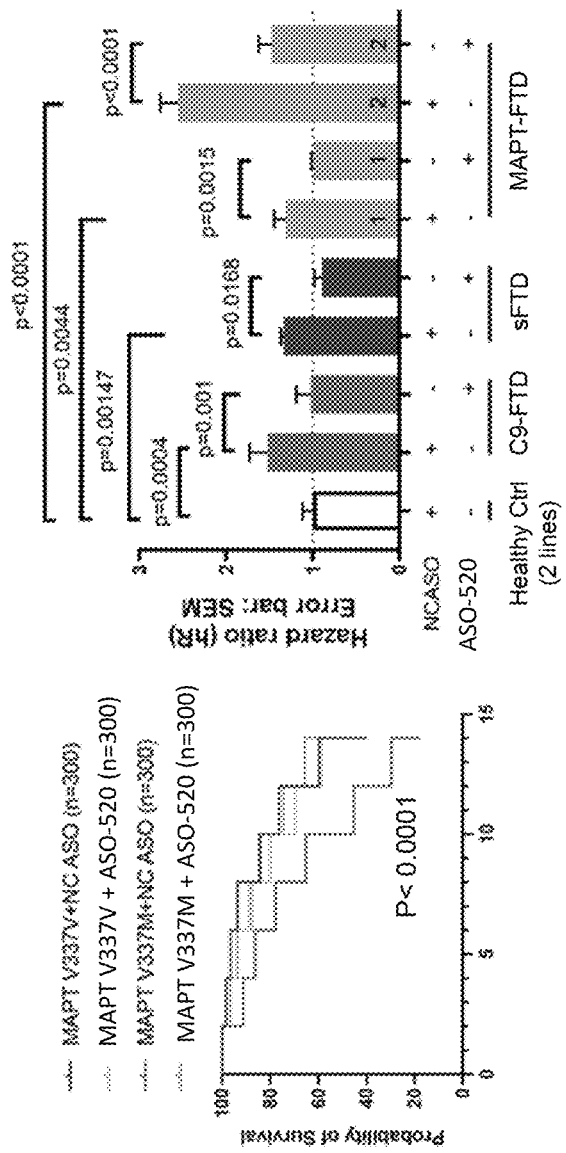
FIG. 5A is a graph showing the probability of survival for FTD patient-derived cortical neurons with MAPT V337V or V337M in the present of NC ASO or AS-520 (SEQ ID NO: 520).
FIG. 5B is a bar graph showing the hazard ratio for cortical neurons from control, C9orf72-associated FTD (C9-FTD), sporadic FTD (sFTD), and microtubule-associated protein tau (MAPT)-associated FTD (MAPT-FTD) patients treated with NC ASO or AS-520.

The ability of FTD patient-derived cortical neurons to survive in the presence of a non-coding ASO or AS-520 (SEQ ID NO: 520) was determined. FIG. 5A is a graph showing the probability of survival for FTD patient-derived cortical neurons with MAPT V337V or V337M in the present of NC ASO or AS-520 (SEQ ID NO: 520). AS-520 increased the probability of survival in MAPT V337M cortical neurons compared to the NC ASO. FIG. 5B is a bar graph showing the hazard ratio for cortical neurons from control, C9orf72-associated FTD (C9-FTD), sporadic FTD (sFTD), and microtubule-associated protein tau (MAPT)-associated FTD (MAPT-FTD) patients treated with NC ASO or AS-520. AS-520 significantly decreased the hazard ratio in the C9-FTD, sFTD and MAPT-FTD cortical neurons.

The disclosure provides ASOs that suppress PIKFYVE expression in human cells. The accompany data suggest that these ASOs may be capable of preventing neurodegeneration in ALS and FTD patients.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention. All references cited herein are incorporated by reference.

The invention claimed is:

1. A single stranded antisense oligonucleotide of 20 nucleotides in length that suppresses the expression of a PIKFYVE, wherein the antisense oligonucleotide comprises a nucleobase sequence that comprises the sequence set forth in SEQ ID NO: 20.

2. The antisense oligonucleotide of claim 1, wherein at least one internucleoside linkage is a modified internucleoside linkage.

3. The antisense oligonucleotide of claim 2, wherein at least one modified internucleoside linkage is a phosphorothioate internucleoside linkage.

4. The antisense oligonucleotide of claim 2, wherein each modified internucleoside linkage is a phosphorothioate internucleoside linkage.

5. The antisense oligonucleotide of claim 1, wherein at least one internucleoside linkage is a phosphodiester internucleoside linkage.

6. The antisense oligonucleotide of claim 5, wherein at least one internucleoside linkage is a phosphorothioate linkage and at least one internucleoside linkage is a phosphodiester linkage.

7. The antisense oligonucleotide of claim 1, wherein at least one nucleoside comprises a modified nucleobase.

8. The antisense oligonucleotide of claim 7, wherein the modified nucleobase is a 5-methylcytosine.

9. The antisense oligonucleotide of claim 1, wherein at least one nucleoside of the antisense oligonucleotide comprises a modified sugar moiety.

10. The antisense oligonucleotide of claim 9, wherein the modified sugar moiety comprises a 2'-O-methoxyethyl group.

11. The antisense oligonucleotide of claim 1, wherein the antisense oligonucleotide is a gapmer.

12. The antisense oligonucleotide of claim 11, wherein the antisense oligonucleotide comprises:

a gap segment consisting of 10 to 12 linked deoxynucleosides;
a 5' wing segment consisting of 4 to 5 linked nucleosides; and
a 3' wing segment consisting of 4 to 5 linked nucleosides, wherein the gap segment is positioned between the 5' wing segment and the 3' wing segment and wherein a nucleoside of each wing segment comprises a modified sugar moiety.

13. The antisense oligonucleotide of claim 12, wherein each nucleoside of each wing segment comprises a modified sugar moiety.

14. The antisense oligonucleotide of claim 12, wherein the nucleosides making up each wing segment comprise at least two different modified sugar moieties.

15. The antisense oligonucleotide of claim 12, wherein the nucleosides making up each wing segment comprise the same modified sugar moiety.

16. The antisense oligonucleotide of claim 13, wherein the modified sugar moiety comprises a 2'-O-methoxyethyl group.

17. A pharmaceutical composition comprising the antisense oligonucleotide of claim 1, and a pharmaceutically acceptable carrier, diluent and/or excipient.

18. The pharmaceutical composition of claim 17, wherein the pharmaceutical composition is formulated for parenteral delivery.

19. The pharmaceutical composition of claim 17, wherein the pharmaceutical composition is formulated for intracerebroventricular injection.

20. The antisense oligonucleotide of claim 1, which comprises the sequence set forth in SEQ ID NO: 520.

21. The antisense oligonucleotide of claim 1, wherein the antisense oligonucleotide suppresses the expression of a PIKFYVE by at least 80%.

22. A single stranded antisense oligonucleotide of 20 nucleotides in length that suppresses the expression of a PIKFYVE, wherein the antisense oligonucleotide has a nucleobase sequence that comprises the sequence set forth in SEQ ID NO: 20, wherein the first 3-5 nucleosides at the 5' end ("5' wing segment") comprise modified sugars, the last 3-5 nucleosides at the 3' end ("3' wing segment") comprise modified sugars, and the remaining nucleosides comprise a gap segment.

23. The antisense oligonucleotide of claim 22, wherein the modified sugars comprise 2'-OMe, 2'-MOE, LNA, or any combination thereof.

24. The antisense oligonucleotide of claim 23, wherein at least one of the modified sugars comprises 2'-OMe.

25. The antisense oligonucleotide of claim 23, wherein at least one of the modified sugars comprises 2'-MOE.

26. The antisense oligonucleotide of claim 23, wherein at least one of the modified sugars comprises LNA.

27. The antisense oligonucleotide of claim 22, wherein the backbone linkages of the 5' wing segment, the 3' wing segment, and the gap segment comprise a mixture of phosphorothioate and phosphodiester linkages.

28. The antisense oligonucleotide of claim 22, which comprises the sequence set forth in SEQ ID NO: 520.

29. A single stranded antisense oligonucleotide of 20 nucleotides in length that suppresses the expression of a PIKFYVE, wherein the antisense oligonucleotide comprises the sequence set forth in SEQ ID NO: 520, wherein the backbone linkage of the antisense oligonucleotide comprises a mixture of phosphorothioate and phosphodiester linkages.

30. The antisense oligonucleotide of claim 29, wherein the first, sixth, seventh, eighth, ninth, tenth, eleventh, twelfth, thirteenth, fourteenth, fifteenth, eighteenth, and nineteenth linkages are phosphorothioate linkages, and the second, third, fourth, fifth, sixteenth, and seventeenth linkages are phosphodiester linkages.

31. The antisense oligonucleotide of claim 22, wherein at least one nucleoside comprises a modified nucleobase.

32. The antisense oligonucleotide of claim 22, wherein the modified nucleobase is a 5-methylcytosine.

33. The antisense oligonucleotide of claim 22, wherein the antisense oligonucleotide comprises a moiety that neutralizes charge on the antisense oligonucleotide.

34. The antisense oligonucleotide of claim 22, wherein the antisense oligonucleotide suppresses the expression of a PIKFYVE by at least 80%.

35. A pharmaceutical composition comprising the antisense oligonucleotide of claim 22, and a pharmaceutically acceptable carrier, diluent and/or excipient.

36. A pharmaceutical composition comprising the antisense oligonucleotide of claim 29, and a pharmaceutically acceptable carrier, diluent and/or excipient.

37. A pharmaceutical composition comprising the antisense oligonucleotide of claim 30, and a pharmaceutically acceptable carrier, diluent and/or excipient.

38. The pharmaceutical composition of claim 36, wherein the pharmaceutical composition is formulated for parenteral delivery or intracerebroventricular injection.

39. The pharmaceutical composition of claim 37, wherein the pharmaceutical composition is formulated for parenteral delivery or intracerebroventricular injection.

* * * * *